United States Patent
Miura et al.

(10) Patent No.: US 12,168,795 B2
(45) Date of Patent: Dec. 17, 2024

(54) METHOD FOR MEASURING CHOLESTEROL IN LOW-DENSITY LIPOPROTEIN, MEASUREMENT REAGENT, AND MEASUREMENT KIT

(71) Applicant: Hitachi Chemical Diagnostics Systems Co., Ltd., Tokyo (JP)

(72) Inventors: Mizuki Miura, Shizuoka (JP); Tomoko Aratake, Shizuoka (JP); Kenta Kinjo, Shizuoka (JP)

(73) Assignee: HITACHI CHEMICAL DIAGNOSTICS SYSTEMS CO., LTD., Tokyo (JP)

( * ) Notice: Subject to any disclaimer, the term of this patent is extended or adjusted under 35 U.S.C. 154(b) by 988 days.

(21) Appl. No.: 16/640,231

(22) PCT Filed: Aug. 30, 2018

(86) PCT No.: PCT/JP2018/032117
§ 371 (c)(1),
(2) Date: Feb. 19, 2020

(87) PCT Pub. No.: WO2019/044973
PCT Pub. Date: Mar. 7, 2019

(65) Prior Publication Data
US 2020/0392558 A1    Dec. 17, 2020

(30) Foreign Application Priority Data
Sep. 1, 2017    (JP) .................. 2017-168235

(51) Int. Cl.
*C12Q 1/60*    (2006.01)
*C12Q 1/32*    (2006.01)
*C12Q 1/44*    (2006.01)

(52) U.S. Cl.
CPC ............... *C12Q 1/60* (2013.01); *C12Q 1/32* (2013.01); *C12Q 1/44* (2013.01); *G01N 2333/902* (2013.01); *G01N 2333/918* (2013.01); *G01N 2405/00* (2013.01)

(58) Field of Classification Search
None
See application file for complete search history.

(56) References Cited

U.S. PATENT DOCUMENTS

| | | |
|---|---|---|
| 6,794,157 B1 | 9/2004 | Sugiuchi |
| 8,685,663 B2 | 4/2014 | Murakami et al. |
| 2005/0170447 A1 | 8/2005 | Lawrence et al. |
| 2009/0023167 A1 | 1/2009 | Miyauchi et al. |
| 2009/0263844 A1 | 10/2009 | Itoh |
| 2010/0041080 A1 | 2/2010 | Aratake et al. |
| 2010/0248276 A1 | 9/2010 | Jumawid et al. |

FOREIGN PATENT DOCUMENTS

| | | | |
|---|---|---|---|
| CA | 2344055 A1 * | 3/2000 | ............... C12Q 1/60 |
| CN | 101120097 A | 2/2008 | |
| EP | 2077333 A1 * | 7/2009 | ............... C12Q 1/60 |
| JP | H109-313200 | 12/1997 | |
| JP | H10-038888 | 2/1998 | |
| JP | H11-030617 | 2/1999 | |
| JP | 2002-202314 | 7/2002 | |
| JP | 2005-137229 | 6/2005 | |
| JP | 2007-523325 | 8/2007 | |
| JP | 2010-246526 | 11/2010 | |
| WO | 2000/017388 | 3/2000 | |
| WO | 2007/026829 | 3/2007 | |
| WO | 2010/055916 | 5/2010 | |
| WO | 2011/136316 | 7/2013 | |

OTHER PUBLICATIONS

Satoiwa et al., "Surfactants Properties of aqueous surfactant solutions (III) B," Properties of the Aqueous Solutions of Surface Active Agents (III) B, Oil Chemistry, 34 (6): 479-487 (1985).

Sugiuchi, et al., "Homogeneous assay for measuring low-density lipoprotein cholesterol in serum with triblock copolymer and a-cyclodextrin sulfate", Clinical Chemistry vol. 44, No. 3 (1998) 522-31.

International Search Report dated Nov. 20, 2018 for PCT/JP2018/032117.

* cited by examiner

*Primary Examiner* — Robert J Yamasaki
*Assistant Examiner* — Charles Zoltan Constantine
(74) *Attorney, Agent, or Firm* — Morgan, Lewis & Bockius LLP

(57) ABSTRACT

To provide a method for simply and precisely measuring cholesterol (LDL-C) in low-density lipoprotein in a sample without use of any surfactant having an alkylphenol structure, in terms of environmental friendliness. A method for measuring LDL-C in a sample, the method comprising: reacting the sample with (i) a combination of cholesterol ester hydrolase and cholesterol oxidase or (ii) a combination of cholesterol ester hydrolase, an oxidized coenzyme and cholesterol dehydrogenase, in an aqueous solvent which comprises: [a] one or more surfactants selected from the group consisting of a polyoxyethylene alkyl ether and a polyoxyethylene polyoxypropylene alkyl ether; and [b] a polyoxyethylene polyoxypropylene copolymer; and which does not comprise any surfactant having an alkylphenol structure; and measuring a substance formed or consumed in the reaction.

18 Claims, No Drawings

METHOD FOR MEASURING CHOLESTEROL IN LOW-DENSITY LIPOPROTEIN, MEASUREMENT REAGENT, AND MEASUREMENT KIT

TECHNICAL FIELD

The present invention relates to a method, a reagent and a kit for measuring cholesterol (hereinafter, abbreviated as LDL-C.) in low-density lipoprotein (hereinafter, referred to as LDL) comprised in a sample.

The present application is a National Phase of PCT/JP2018/032117 filed Aug. 30, 2018, which in turn claims the priority based on Japanese Patent Application No. 2017-168235 filed in Japan on Sep. 1, 2017, the contents of which are herein incorporated by reference.

BACKGROUND ART

LDL plays a role of supplying cholesterol to peripheral cells, and it is a direct factor for various types of arteriosclerosis such as coronary arteriosclerotic disease. An increase in LDL-C is one principal risk factor for arteriosclerotic disease, and fractional determination of such LDL-C is clinically useful.

Conventional methods for quantitatively determining LDL-C include an ultracentrifugation method, an electrophoresis, and a calculation method with a Friedewald formula. The ultracentrifugation method is a method comprising separating LDL by using an ultracentrifuge by means of the difference in specific gravity between lipoproteins and then measuring the amount of the cholesterol (Non-patent Document 1). A separation step according to the ultracentrifugation method, however, is complicated, and has disadvantages in terms of promptness, simplicity, and the like. Examples of the electrophoresis include a method comprising separation with an agarose gel as a supporting medium by means of the difference in charge between lipoproteins, and a method comprising separation with a polyacrylamide gel as a supporting medium by means of the difference in particle size between lipoproteins. The electrophoresis, however, is poor in quantitative capability, and has problems in terms of simplicity, economic efficiency, and the like. The calculation method with a Friedewald formula, which comprises calculating the amount of LDL-C from the measurement values of total cholesterol (hereinafter, abbreviated as T-C.), cholesterol (hereinafter, abbreviated as HDL-C.) in high-density lipoprotein (hereinafter, referred to as HDL), and total triglyceride (hereinafter, abbreviated as T-TG.), according to the following calculation formula (Non-patent Document 2), is affected by the content of T-TG in the serum, and/or the diet, and thus has any problem in terms of accuracy.

(LDL-C)=(T-C)−(HDL-C)−(T-TG)/5

In recent years, methods for quantitatively determining LDL-C have also been reported which do not require any separation step such as an ultracentrifugation method and which can be applied to general-purpose auto-analyzers.

In particular, the following methods are known as such methods for quantitatively determining LDL-C.

A method for quantitatively determining LDL-C in a test sample, the method consisting of a first step of allowing cholesterol esterase and cholesterol oxidase to act in the presence of a surfactant acting on any lipoprotein other than LDL, and removing hydrogen peroxide generated, to thereby remove cholesterol in each lipoprotein of HDL, very low-density lipoprotein (hereinafter, referred to as VLDL) and chylomicron in a test sample, and then a second step of quantitatively determining the remaining cholesterol in the test sample (Patent Document 1).

A method for quantitatively determining LDL-C, comprising adding a surfactant selected from polyoxyethylene alkylene phenyl ether and polyoxyethylene alkylene tribenzyl phenyl ether, and an enzyme reagent for measuring cholesterol to the serum and preferentially reacting them with cholesterols in HDL and VLDL, among cholesterols in lipoproteins, and then measuring the reaction amount of the remaining cholesterol (Patent Document 2).

A method comprising adding a polyoxyethylene derivative and a polyoxyethylene-polyoxypropylene copolymer, and an enzyme for measuring cholesterol to a biological sample, and selectively measuring LDL-C among cholesterols in lipoproteins (Patent Document 3).

A method for measuring LDL-C, characterized in that a biological sample is subjected to measurement in the presence of dimethyl-α-cyclodextrin and/or poly-β-cyclodextrin (Patent Document 4).

A method for directly and selectively measuring cholesterol in a sample comprising any one or more of chylomicron, HDL, LDL and VLDL, in which LDL-C in the sample is quantitatively determined in the presence of a compound containing phospholipid or a phospholipid-like group (Patent Document 5).

A method for measuring cholesterol in low-density lipoprotein in a sample, characterized in that a sample and an enzyme for measuring cholesterol are reacted in the presence of

[a] polyoxyethylene-polyoxyalkylene alkylaryl ether;
[b] one or more surfactants selected from the group consisting of a polyoxyethylene-polyoxyalkylene copolymer, polyoxyethylene alkenyl ether, polyoxyethylene branched alkyl ether and polyoxyethylene-polyoxyalkylene branched alkyl ether;
[c] one or more surfactants selected from the group consisting of a primary amine, a secondary amine, a tertiary amine, and a quaternary ammonium; and
[d] a polyanion, and
a substance formed or a substance consumed in the reaction is measured (Patent Document 6).

In recent years, it has been reported that alkylphenols such as octylphenol have endocrine-disrupting action, and production of a surfactant having an alkylphenol structure, such as polyoxyethylene alkylphenyl ether, and use thereof for reagents have been gradually avoided in terms of environmental friendliness.

Not only normal samples, but also various abnormal samples are often used as samples in clinical examinations. A problem is that there is any sample rich in lipid as one of such abnormal samples and turbidity due to such lipid has any influence on measurement.

PRIOR ART DOCUMENTS

Patent Documents

Patent Document 1: Japanese unexamined Patent Application Publication No. 10-38888
Patent Document 2: Japanese unexamined Patent Application Publication No. 9-313200
Patent Document 3: WO 2000/17388
Patent Document 4: Japanese unexamined Patent Application Publication No. 11-30617

Patent Document 5: Japanese unexamined Patent Application Publication No. 2002-202314
Patent Document 6: WO 2010/55916

Non-Patent Documents

Non-patent Document 1: Advanced Lipid Research (Adv. Lipid Res.), Vol. 6, p. 1, 1968
Non-patent Document 2: Clinical Chemistry (Clin. Chem.), Vol. 18, p. 499, 1972

SUMMARY OF THE INVENTION

Object to be Solved by the Invention

An object of the present invention is to provide a method, a reagent and a kit for simply and precisely measuring LDL-C in a sample without use of any surfactant having an alkylphenol structure, such as polyoxyethylene alkylphenyl ether, in terms of environmental friendliness.

Another object of the present invention is to provide a method, a reagent and a kit for simply and precisely measuring LDL-C in a sample without use of any surfactant having an alkylphenol structure, such as polyoxyethylene alkylphenyl ether and without any influence of turbidity due to lipid.

Means to Solve the Object

The present inventors have made intensive studies about a method for measuring LDL-C, and as a result, have found that LDL-C in a sample can be simply and precisely measured without any removal of cholesterol in lipoprotein other than LDL and any physical fractionation operation of lipoprotein, by reacting the sample with a combination of cholesterol ester hydrolase and cholesterol oxidase or a combination of cholesterol ester hydrolase, an oxidized coenzyme and cholesterol dehydrogenase in an aqueous solvent which comprises a combination of specific surfactants other than a surfactant having an alkylphenol structure and which does not comprise any surfactant having an alkylphenol structure, thereby leading to completion of the present invention.

The present inventors have further made intensive studies about a method for measuring LDL-C, and as a result, have found that LDL-C in a sample can be simply and precisely measured without any removal of cholesterol in lipoprotein other than LDL and any physical fractionation operation of lipoprotein and furthermore without any influence of turbidity due to lipid, by reacting the sample with a combination of cholesterol ester hydrolase and cholesterol oxidase or a combination of cholesterol ester hydrolase, an oxidized coenzyme and cholesterol dehydrogenase, in an aqueous solvent which comprises a combination of specific surfactants other than a surfactant having an alkylphenol structure, and a polyoxypropylene derivative not comprising any polyoxyethylene in a molecule, and which does not comprise any surfactant having an alkylphenol structure, thereby leading to completion of the present invention.

That is, the present invention relates to the following (1) to (24).
(1) A method for measuring LDL-C in a sample, the method comprising:
reacting the sample with (i) a combination of cholesterol ester hydrolase and cholesterol oxidase or (ii) a combination of cholesterol ester hydrolase, an oxidized coenzyme and cholesterol dehydrogenase, in an aqueous solvent which comprises
[a] one or more surfactants selected from the group consisting of a polyoxyethylene alkyl ether (hereinafter, abbreviated as POE alkyl ether) and a polyoxyethylene polyoxypropylene alkyl ether (hereinafter, abbreviated as POEPOP alkyl ether); and
[b] a polyoxyethylene polyoxypropylene copolymer (hereinafter, abbreviated as POEPOP copolymer), and which does not comprise any surfactant having an alkylphenol structure; and
measuring a substance formed or consumed in the reaction.
(2) The method according to (1), wherein the alkyl in [a] the POE alkyl ether and the POEPOP alkyl ether is an alkyl having 8 to 20 carbon atoms.
(3) The method according to (1) or (2), wherein the aqueous solvent further comprises [c] a polyoxypropylene derivative not comprising any polyoxyethylene in a molecule.
(4) The method according to (3), wherein [c] the polyoxypropylene derivative not comprising any polyoxyethylene in a molecule is a polypropylene glycol or a polyoxypropylene glyceryl ether.
(5) The method according to any one of (1) to (4), wherein the substance formed is a hydrogen peroxide.
(6) The method according to (5), wherein the hydrogen peroxide is measured by using a reagent for measuring hydrogen peroxide.
(7) The method according to any one of (1) to (4), wherein the substance formed is a reduced coenzyme.
(8) The method according to (7), wherein the reduced coenzyme is measured by using a reagent for measuring a reduced coenzyme.
(9) A reagent for measuring LDL-C in a sample, the reagent comprising:
[a] one or more surfactants selected from the group consisting of POE alkyl ether and POEPOP alkyl ether;
[b] a POEPOP copolymer; and
a cholesterol ester hydrolase and a cholesterol oxidase; and
not comprising any surfactant having an alkylphenol structure.
(10) The reagent according to (9), further comprising a reagent for measuring a substance formed as a result of the reaction of cholesterol ester hydrolase and cholesterol oxidase with the sample.
(11) The reagent according to (10), wherein the substance formed as a result of the reaction of cholesterol ester hydrolase and the cholesterol oxidase with the sample is a hydrogen peroxide.
(12) A reagent for measuring cholesterol in low-density lipoprotein in a sample, the reagent comprising:
[a] one or more surfactants selected from the group consisting of POE alkyl ether and POEPOP alkyl ether;
[b] a POEPOP copolymer; and
a cholesterol ester hydrolase, an oxidized coenzyme and a cholesterol dehydrogenase.
(13) The reagent according to (12), further comprising a reagent for measuring a substance formed as a result of the reaction of the cholesterol ester hydrolase, the oxidized coenzyme and the cholesterol dehydrogenase with the sample.
(14) The reagent according to (13), wherein the substance as a result of the reaction of the cholesterol ester hydrolase, the oxidized coenzyme and the cholesterol dehydrogenase with the sample is a reduced coenzyme.

(15) The reagent according to any one of (9) to (14), wherein alkyl in [a] the POE alkyl ether and the POEPOP alkyl ether is an alkyl having 8 to 20 carbon atoms.

(16) The reagent according to any one of (9) to (15), further comprising [c] a polyoxypropylene derivative not comprising any polyoxyethylene in a molecule.

(17) The reagent according to (16), wherein [c] the polyoxypropylene derivative not comprising any polyoxyethylene in a molecule is a polypropylene glycol or a polyoxypropylene glyceryl ether.

(18) A kit for measuring LDL-C in a sample, the kit comprising:
a first reagent comprising a reagent for measuring hydrogen peroxide, and a second reagent comprising cholesterol oxidase, wherein
[a] one or more surfactants selected from the group consisting of POE alkyl ether and POEPOP alkyl ether;
[b] a POEPOP copolymer; and
a cholesterol ester hydrolase are each comprised in either the first or second reagent, or in both of the first and second reagents, and no surfactant having an alkylphenol structure is comprised in either the first or second reagent.

(19) The kit according to (18), further comprising a reagent for measuring hydrogen peroxide, in the second reagent.

(20) A kit for measuring LDL-C in a sample, the kit comprising:
a first reagent comprising an oxidized coenzyme, and a second reagent comprising a cholesterol dehydrogenase, wherein
[a] one or more surfactants selected from the group consisting of POE alkyl ether and POEPOP alkyl ether;
[b] a POEPOP copolymer; and
a cholesterol ester hydrolase are each comprised in either the first or second reagent, or in both of the first and second reagents, and no surfactant having an alkylphenol structure is comprised in either the first or second reagent.

(21) The kit according to (20), further comprising a reagent for measuring a reduced coenzyme in either the first or second reagent, or in both of the first and second reagents.

(22) The kit according to any one of (18) to (21), wherein alkyl in [a] the POE alkyl ether and the POEPOP alkyl ether is an alkyl having 8 to 20 carbon atoms.

(23) The kit according to any one of (18) to (22), further comprising [c] a polyoxypropylene derivative not comprising any polyoxyethylene in a molecule, in either the first or second reagent, or in both of the first and second reagents.

(24) The kit according to (23), wherein [c] the polyoxypropylene derivative not comprising any polyoxyethylene in a molecule is a polypropylene glycol or a polyoxypropylene glyceryl ether.

Effect of the Invention

The present invention provides a method, a reagent and a kit for simply and precisely measuring LDL-C in a sample without use of any surfactant having an alkylphenol structure, such as polyoxyethylene alkylphenyl ether.

The present invention further provides a method, a reagent and a kit for simply and precisely measuring LDL-C in a sample without use of any surfactant having an alkylphenol structure, such as polyoxyethylene alkylphenyl ether and without any influence of turbidity due to lipid.

MODE OF CARRYING OUT THE INVENTION

1. Method for Measuring LDL-C

The method for measuring LDL-C of the present invention is a method for measuring LDL-C in a sample by use of an enzyme for measuring cholesterol, in which LDL-C in a sample is measured without use of any surfactant having an alkylphenol structure. The method for measuring LDL-C of the present invention is also a method for measuring LDL-C in a sample without requiring any fractionation operation of lipoprotein by a physical method such as centrifugation and without any removal of cholesterol in lipoprotein other than LDL in a sample before measurement of LDL-C. The enzyme for measuring cholesterol means a cholesterol ester hydrolase, a cholesterol oxidase, an oxidized coenzyme, or a cholesterol dehydrogenase.

The method for measuring LDL-C of the present invention is a method characterized by reacting the sample with (i) a combination of a cholesterol ester hydrolase and a cholesterol oxidase or (ii) a combination of a cholesterol ester hydrolase, an oxidized coenzyme and a cholesterol dehydrogenase, in an aqueous solvent which comprises
[a] one or more surfactants selected from the group consisting of POE alkyl ether and POEPOP alkyl ether; and
[b] a POEPOP copolymer, and
which does not comprise any surfactant having an alkylphenol structure, and measuring a substance formed or consumed in the reaction, in which the method comprises the following steps.

[1] A step of reacting the sample with (i) a combination of a cholesterol ester hydrolase and a cholesterol oxidase or (ii) a combination of a cholesterol ester hydrolase, an oxidized coenzyme and a cholesterol dehydrogenase, in an aqueous solvent which comprises
[a] one or more surfactants selected from the group consisting of POE alkyl ether and POEPOP alkyl ether; and
[b] a POEPOP copolymer, and
which does not comprise any surfactant having an alkylphenol structure;

[2] a step of measuring a substance formed or consumed in the aforementioned step [1];

[3] a step of correlating a calibration curve showing a relationship between the concentration of LDL-C and the amount of information derived from the substance formed or consumed, created in advance by performing the [1] and [2] by use of a sample where the concentration of LDL-C is known, with the measurement value in the aforementioned [2]; and

[4] a step of determining in the concentration of LDL-C in the sample.

The method for measuring LDL-C of the present invention is also a method characterized by reacting the sample with (i) a combination of a cholesterol ester hydrolase and a cholesterol oxidase or (ii) a combination of a cholesterol ester hydrolase, an oxidized coenzyme and a cholesterol dehydrogenase, in an aqueous solvent which comprises
[a] one or more surfactants selected from the group consisting of POE alkyl ether and POEPOP alkyl ether;
[b] a POEPOP copolymer; and
[c] a polyoxypropylene derivative not comprising any polyoxyethylene in a molecule, and which does not comprise any surfactant having an alkylphenol structure, and measuring a substance formed or consumed in the reaction, in which the method comprises the following steps.

[1] A step of reacting the sample with (i) a combination of a cholesterol ester hydrolase and a cholesterol oxidase or (ii) a combination of a cholesterol ester hydrolase, an oxidized coenzyme and a cholesterol dehydrogenase, in an aqueous solvent which comprises
[a] one or more surfactants selected from the group consisting of POE alkyl ether and POEPOP alkyl ether;
[b] a POEPOP copolymer; and
[c] a polyoxypropylene derivative not comprising any polyoxyethylene in a molecule, and which does not comprise any surfactant having an alkylphenol structure;
[2] a step of measuring a substance formed or consumed in the aforementioned step [1];
[3] a step of correlating a calibration curve showing a relationship between the concentration of LDL-C and the amount of information derived from the substance formed or consumed, created in advance by performing the [1] and [2] by use of a sample where the concentration of LDL-C is known, with the measurement value in the aforementioned [2]; and
[4] a step of determining in the concentration of LDL-C in the sample.

The aqueous solvent for use in the present invention is not particularly limited as long as such a solvent is an aqueous solvent which enables the method for measuring LDL-C of the present invention, and examples thereof include deionized water, distilled water, and a buffer solution, preferably a buffer solution.

The pH in the method for measuring LDL-C of the present invention may be any pH as long as such a pH is any pH which enables the method for measuring LDL-C of the present invention, and is, for example, a pH of 4 to 10. In the case of use of a buffer solution as the aqueous solvent, any buffer is desirably used depending on the pH set. Examples of the buffer for use in the buffer solution include a tris (hydroxymethyl)aminomethane buffer, a phosphate buffer, a borate buffer, and a Good's buffer.

Examples of such a Good's buffer include 2-morpholinoethanesulfonic acid (MES), bis(2-hydroxyethyl)iminotris(hydroxymethyl)methane (Bis-Tris), N-(2-acetamide)iminodiacetic acid (ADA), piperazine-N,N'-bis(2-ethanesulfonic acid) (PIPES), N-(2-acetamide)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

The concentration of such a buffer solution is not particularly limited as long as the concentration is any concentration suitable for measurement, and is preferably 0.001 to 2.0 mol/L, more preferably 0.005 to 1.0 mol/L.

Examples of the substance formed in a reaction of a sample with (i) a combination of a cholesterol ester hydrolase and a cholesterol oxidase in the method for measuring LDL-C of the present invention include hydrogen peroxide, and examples of the substance formed in a reaction of a sample with (ii) a combination of a cholesterol ester hydrolase, an oxidized coenzyme and a cholesterol dehydrogenase include a reduced coenzyme. Examples of the substance consumed in a reaction of a sample with (i) a combination of a cholesterol ester hydrolase and a cholesterol oxidase include an oxygen molecule, and examples of the substance consumed in a reaction of a sample with (ii) a combination of a cholesterol ester hydrolase, an oxidized coenzyme and a cholesterol dehydrogenase include an oxidized coenzyme. The hydrogen peroxide formed can be measured by using, for example, a hydrogen peroxide electrode, or a reagent for measuring hydrogen peroxide, described below. The reduced coenzyme formed can be measured according to, for example, a method for measuring an absorbance of the reduced coenzyme, or a method using a reagent for measuring a reduced coenzyme, described below. The oxygen molecule consumed can be measured by using, for example, an oxygen electrode. The oxidized coenzyme consumed can be measured with, for example, an absorbance at an absorption wavelength of the oxidized coenzyme.

Examples of the sample for use in the method for measuring LDL-C of the present invention include whole blood, plasma, and serum, preferably plasma and serum. Not only a sample derived from a healthy individual, but also a sample rich in lipid can be used in the method for measuring of the present invention. Examples of the sample rich in lipid include a high-TG sample high in triglyceride (TG).

The cholesterol ester hydrolase in the present invention is not particularly limited as long as it is an enzyme having the ability to hydrolyze cholesterol ester, and, for example, not only a cholesterol esterase or a lipoprotein lipase derived from any animal, plant or microorganism, but also a cholesterol esterase or a lipoprotein lipase produced by a genetic engineering method can be used.

Not only unmodified cholesterol ester hydrolase, but also chemically modified cholesterol ester hydrolase can be used as the cholesterol ester hydrolase. A commercially available product can also be used as the cholesterol ester hydrolase.

Examples of commercially available cholesterol ester hydrolase include cholesterol esterase (COE-311; manufactured by Toyobo Co., Ltd.), lipoprotein lipase (LPL-311; manufactured by Toyobo Co., Ltd.), and cholesterol esterase "Amano" 2 (CHE-2; manufactured by Amano Enzyme Inc.). Such cholesterol ester hydrolase can also be used in combinations of two or more kinds thereof, in the present invention.

Examples of a group (chemically modifying group) for modifying the cholesterol ester hydrolase in chemical modification of such an enzyme include a group comprising polyethylene glycol as a main component, a group comprising polypropylene glycol as a main component, a group having a copolymer of polypropylene glycol and polyethylene glycol, a group comprising water-soluble polysaccharide, a sulfopropyl group, a sulfobutyl group, a polyurethane group, and a group having a chelating function, and a group comprising polyethylene glycol as a main component is preferable. Examples of such water-soluble polysaccharide include dextran, pullulan, and soluble starch.

Examples of a reagent (chemical modifier) for chemically modifying the cholesterol ester hydrolase include a compound simultaneously having the aforementioned chemically modifying group, and a functional group or structure reactable with an amino group, a carboxyl group, a sulfhydryl group or the like in the enzyme. Examples of the functional group or structure reactable with an amino group in the enzyme include a carboxyl group, an active ester group (N-hydroxysuccinimide group and the like), an acid anhydride, an acid chloride, aldehyde, an epoxide group, 1,3-propane sultone, and 1,4-butane sultone. Examples of the functional group or structure reactable with a carboxyl group in the enzyme include an amino group. Examples of the group or structure reactable with a sulfhydryl group in the enzyme include a maleimide group, disulfide, and α-haloester (α-iodoester and the like).

A commercially available product can also be used as the chemical modifier. Examples of such a commercially available chemical modifier include Sunbright VFM-4101, Sunbright ME-050AS, and Sunbright DE-030AS (all are manufactured by NOF Corporation) each having a group comprising polyethylene glycol as a main component and an N-hydroxysuccinimide group, Sunbright AKM series (for example, Sunbright AKM-1510) each having a group comprising polyalkylene glycol as a main component and an acid anhydride structure, Sunbright ADM series and Sunbright ACM series (all are manufactured by NOF Corporation), EPDX-3400 and M-EPDX-5000 (all are manufactured by Shearwater Polymers, Inc.) each having a group comprising polyethylene glycol as a main component and an epoxide group, and diethylenetriamine-N,N,N',N",N"-pentaacetic acid dianhydride (DTPA anhydride; manufactured by Dojindo Laboratories) having a group having a chelating function and an acid anhydride structure.

The chemical modification of the cholesterol ester hydrolase can be performed by, for example, the following method, but is not limited to such a method. First, the cholesterol ester hydrolase is dissolved in a buffer solution (for example, HEPES buffer solution) having a pH of 8.0 or more, the chemical modifier is added in an amount of 0.01 to 500 times by mole at 0 to 55° C., and the resultant is stirred for 5 minutes to 5 hours. The chemically modified cholesterol ester hydrolase which can be used in such an enzyme reaction is not only such a reaction liquid by itself, but also any one from which an unreacted chemical modifier and the like are, if necessary, removed with an ultrafilter membrane or the like.

The concentration of the cholesterol ester hydrolase in the method for measuring LDL-C of the present invention is not particularly limited as long as it is any concentration which enables the method for measuring LDL-C of the present invention, and the concentration in the reaction liquid is usually 0.001 to 800 kU/L, preferably 0.01 to 300 kU/L.

The cholesterol oxidase in the present invention is not particularly limited as long as it is an enzyme having the ability to oxidize cholesterol to thereby form hydrogen peroxide, and, for example, not only cholesterol oxidase derived from any animal, plant or microorganism, but also cholesterol oxidase produced by a genetic engineering method can be used, and a commercially available product such as cholesterol oxidase (CHODI; manufactured by Kikkoman Corporation), cholesterol oxidase (CHO-CE; manufactured by Kikkoman Corporation), or cholesterol oxidase (COO-321; manufactured by Toyobo Co., Ltd.) can also be used. Such cholesterol oxidase can also be used in combinations of two or more kinds thereof, in the present invention.

The cholesterol oxidase may be an unmodified enzyme or a chemically modified enzyme. The chemically modified cholesterol oxidase can be made by, for example, using the above chemical modifier according to the above chemical modification method.

The concentration of the cholesterol oxidase in the method for measuring LDL-C of the present invention is not particularly limited as long as it is any concentration which enables the method for measuring LDL-C of the present invention, and the concentration in the reaction liquid is usually 0.001 to 800 kU/L, preferably 0.01 to 300 kU/L.

The cholesterol dehydrogenase in the present invention is not particularly limited as long as it is an enzyme having the ability to oxidize cholesterol in the presence of an oxidized coenzyme to thereby form a reduced coenzyme, and, for example, not only cholesterol dehydrogenase derived from any animal, plant or microorganism, but also cholesterol dehydrogenase produced by a genetic engineering method can be used. A commercially available product such as cholesterol dehydrogenase "Amano" 5 (CHDH-5; manufactured by Amano Enzyme Inc.) can also be used. Such cholesterol dehydrogenase can also be used in combinations of two or more kinds thereof, in the present invention. The cholesterol dehydrogenase may be an unmodified enzyme or a chemically modified enzyme. The chemically modified cholesterol dehydrogenase can be made by, for example, using the above chemical modifier according to the above chemical modification method.

The concentration of the cholesterol dehydrogenase in the method for measuring LDL-C of the present invention is not particularly limited as long as it is any concentration which enables the method for measuring LDL-C of the present invention, and the concentration in the reaction liquid is usually 0.001 to 800 kU/L, preferably 0.01 to 300 kU/L.

An oxidized coenzyme is used in a measurement method using the cholesterol dehydrogenase in the present invention. Examples of the oxidized coenzyme include NAD, NADP, thio-NAD, and thio-NADP. The concentration of the oxidized coenzyme is not particularly limited as long as it is any concentration which enables the method for measuring LDL-C of the present invention, and is preferably 0.01 to 10 g/L.

Examples of the surfactant having an alkylphenol structure in the present invention include polyoxyethylene alkylphenyl ether (hereinafter, abbreviated as POE alkylphenyl ether) and polyoxyethylene polyoxypropylene alkylphenyl ether (hereinafter, abbreviated as POEPOP alkylphenyl ether). Examples of alkyl in the POE alkylphenyl ether and the POEPOP alkylphenyl ether include octyl and nonyl.

Specific examples of the POE alkylphenyl ether include Triton X-100 (POE octylphenyl ether; manufactured by Sigma-Aldrich Co. LLC.).

Specific examples of the POEPOP alkylphenyl ether include Emulgen L40 (manufactured by Kao Corporation) and Acronecess KP189R (manufactured by NOF Corporation).

Examples of such alkyl in the POE alkyl ether and the POEPOP alkyl ether for use in the present invention include an alkyl having 8 to 20 carbon atoms, preferably an alkyl having 9 to 18 carbon atoms, more preferably an alkyl having 9 to 16 carbon atoms, particularly preferably an alkyl having 10 to 13 carbon atoms. Examples of the alkyl having 8 to 20 carbon atoms include octyl, isooctyl, nonyl, isononyl, decyl, isodecyl, undecyl, isoundecyl, dodecyl (lauryl), isododecyl, tridecyl, isotridecyl, tetradecyl (myristyl), isotetradecyl, pentadecyl, isopentadecyl, hexadecyl (cetyl), isohexadecyl, heptadecyl, isoheptadecyl, octadecyl (stearyl), isooctadecyl, nonadecyl, isononadecyl, icosyl, and isoicosyl. Examples of the alkyl having 9 to 18 carbon atoms include nonyl, isononyl, decyl, isodecyl, undecyl, isoundecyl, dodecyl (lauryl), isododecyl, tridecyl, isotridecyl, tetradecyl (myristyl), isotetradecyl, pentadecyl, isopentadecyl, hexadecyl (cetyl), isohexadecyl, heptadecyl, isoheptadecyl, octadecyl (stearyl), and isooctadecyl. Examples of the alkyl having 9 to 16 carbon atoms include nonyl, isononyl, decyl, isodecyl, undecyl, isoundecyl, dodecyl (lauryl), isododecyl, tridecyl, isotridecyl, tetradecyl (myristyl), isotetradecyl, pentadecyl, isopentadecyl, hexadecyl (cetyl), and isohexadecyl. Examples of the alkyl having 10 to 13 carbon atoms include decyl, isodecyl, undecyl, isoundecyl, dodecyl (lauryl), isododecyl, tridecyl, and isotridecyl. A polymerization mode of POEPOP in the POEPOP alkyl ether is not particularly limited, and examples thereof include a block or a random polymerization. Examples of such a block polymerization include a diblock copolymer, a triblock copolymer, and a tetrablock copolymer.

Specific examples of the POE alkyl ether include Finesurf D-35, Finesurf D-45, Finesurf D-60, Finesurf D-65, Finesurf D-85, Safetycut ID-1033 and Safetycut ID-1087 (all are POE isodecyl ethers; manufactured by Aoki Oil Industrial Co., Ltd.), Finesurf TD-30, Finesurf TD-50, Finesurf TD-70, Finesurf TD-80, Finesurf TD-85, Finesurf TD-90, Finesurf TD-100, Finesurf TD-120, Finesurf TD-150 and Finesurf TD-200 (all are POE tridecyl ethers; manufactured by Aoki Oil Industrial Co., Ltd.), NIKKOL BL-2, NIKKOL BL-4.2, NIKKOL BL-9EX, NIKKOL BL-21 and NIKKOL BL-25 (all are POE lauryl ethers; manufactured by Nikko Chemicals Co., Ltd.), NIKKOL BC-2, NIKKOL BC-5.5, NIKKOL BC-7, NIKKOL BC-10, NIKKOL BC-15, NIKKOL BC-20, NIKKOL BC-23, NIKKOL BC-25, NIKKOL BC-30 and NIKKOL BC-40 (all are POE cetyl ethers; manufactured by Nikko Chemicals Co., Ltd.), EMALEX 703, EMALEX 705, EMALEX 707, EMALEX 709, EMALEX 710, EMALEX 712, EMALEX 715, EMALEX 720, EMALEX 725, EMALEX 730 and EMALEX 750 (all are POE lauryl ethers; manufactured by Nihon Emulsion Co., Ltd.), EMALEX 102, EMALEX 103, EMALEX 104, EMALEX 105, EMALEX 107, EMALEX 112, EMALEX 115, EMALEX 117, EMALEX 120, EMALEX 125 and EMALEX 130 (all are POE cetyl ethers; manufactured by Nihon Emulsion Co., Ltd.), Nonion ID-203, Nonion ID-206 and Nonion ID-209 (all are POE isodecyl ethers; manufactured by NOF Corporation), Nonion K-204, Nonion K-220 and Nonion K-230 (all are POE lauryl ethers; manufactured by NOF Corporation), and Nonion P-208, Nonion P-210 and Nonion P-213 (all are POE cetyl ethers; manufactured by NOF Corporation).

Specific examples of the POEPOP alkyl ether include Wondersurf NDR-800, Wondersurf NDR-1000 and Wondersurf NDR-1400 (all are POEPOP decyl ethers; manufactured by Aoki Oil Industrial Co., Ltd.), Wondersurf ID-50, Wondersurf ID-70, Wondersurf ID-90, Finesurf IDEP-608, Finesurf IDEP-604 and Finesurf IDEP-802 (all are POEPOP isodecyl ethers; manufactured by Aoki Oil Industrial Co., Ltd.), Wondersurf RL-80, Wondersurf RL-100, Wondersurf RL-140, Wondersurf 80, Wondersurf 100 and Wondersurf 140 (all are POEPOP lauryl ethers; manufactured by Aoki Oil Industrial Co., Ltd.), Wondersurf S-800, Wondersurf S-1000, Wondersurf S-1400, Finesurf TDP-0633K, Finesurf TDE-1033 and Finesurf TDE-1055 (all are POEPOP tridecyl ethers; manufactured by Aoki Oil Industrial Co., Ltd.), NIKKOL PBC-31, NIKKOL PBC-33, NIKKOL PBC-34 and NIKKOL PBC-44 (all are POEPOP cetyl ethers; manufactured by Nikko Chemicals Co., Ltd.), and EMALEX DAPE-0203, EMALEX DAPE-0205, EMALEX DAPE-0207, EMALEX DAPE-0210, EMALEX DAPE-0212, EMALEX DAPE-0215, EMALEX DAPE-0220 and EMALEX DAPE-0230 (all are POEPOP decyl ethers; manufactured by Nihon Emulsion Co., Ltd.).

The concentration of the POE alkyl ether in the method for measuring LDL-C of the present invention is not particularly limited as long as it is any concentration which enables the method for measuring LDL-C of the present invention, and the concentration in the reaction liquid is usually 0.0001 to 20% (w/v), preferably 0.001 to 5% (w/v).

The concentration of the POEPOP alkyl ether in the method for measuring LDL-C of the present invention is not particularly limited as long as it is any concentration which enables the method for measuring LDL-C of the present invention, and the concentration in the reaction liquid is usually 0.0001 to 20% (w/v), preferably 0.001 to 5% (w/v).

A polymerization mode of POEPOP in the POEPOP copolymer is not particularly limited, and examples thereof include a block or a random polymerization. Examples of such a block polymerization include a diblock copolymer, a triblock copolymer, and a tetrablock copolymer. The molecular weight of POP is 500 to 7000, preferably 1000 to 6000. The molecular weight of the POEPOP copolymer is 600 to 12000, preferably 1500 to 8000.

Specific examples of the POEPOP copolymer include Pluronic L-101, Pluronic L-121, Pluronic P-103 and Pluronic F-108 (all are manufactured by ADEKA Corporation), and Pronon 201, Pronon 204 and Pronon 208 (all are manufactured by NOF Corporation).

The concentration of the POEPOP copolymer in the method for measuring LDL-C of the present invention is not particularly limited as long as it is any concentration which enables the method for measuring LDL-C of the present invention, and the concentration in the reaction liquid is usually 0.0001 to 20% (w/v), preferably 0.001 to 5% (w/v).

The polyoxypropylene derivative not comprising any polyoxyethylene in a molecule in the present invention is not particularly limited as long as it is a polyoxypropylene derivative not comprising any polyoxyethylene in a molecule, which enables the method for measuring LDL-C of the present invention, and examples thereof include polypropylene glycol and polyoxypropylene glyceryl ether. The molecular weight of the polyoxypropylene derivative not comprising any polyoxyethylene in a molecule in the present invention is not particularly limited as long as it is any molecular weight which enables the method for measuring LDL-C of the present invention, and is usually 500 to 4000, preferably 1000 to 3500, particularly preferably 1200 to 3000.

Specific examples of the polyoxypropylene derivative not comprising any polyoxyethylene in a molecule include Uniol D-700, Uniol D-1000, Uniol D-1200, Uniol D-2000 and Uniol D-4000 (all are polypropylene glycols; manufactured by NOF Corporation), Uniol TG-1000R and Uniol TG-3000 (all are polyoxypropylene glyceryl ethers; manufactured by NOF Corporation), and polypropylene glycol diol type 1,000, polypropylene glycol diol type 2,000 and polypropylene glycol diol type 3,000 (all are polypropylene glycol; manufactured by Wako Pure Chemical Industries, Ltd.).

The concentration of the polyoxypropylene derivative not comprising any polyoxyethylene in a molecule, in the method for measuring LDL-C of the present invention, is not particularly limited as long as it is any concentration which enables the method for measuring LDL-C of the present invention, and the concentration in the reaction liquid is usually 0.0001 to 5% (w/v), preferably 0.001 to 1% (w/v).

The reaction temperature in the method for measuring LDL-C of the present invention is not particularly limited as long as it is any temperature which enables the method for measuring LDL-C of the present invention, and is preferably 10 to 50° C., more preferably 30 to 40° C. A reaction temperature set in a general-purpose auto-analyzer is usually 37° C.

The reaction time in the method for measuring LDL-C of the present invention is not particularly limited as long as it is any reaction time which enables the method for measuring LDL-C of the present invention, and is preferably 1 to 60 minutes, more preferably 2 to 30 minutes.

Measurement of LDL-C in the method for measuring LDL-C of the present invention can be performed by, for example, measuring hydrogen peroxide or a reduced coenzyme formed by a reaction. Such measurement can also be performed by measuring the amount of oxygen consumed in a reaction.

The amount of hydrogen peroxide formed can be measured by using, for example, a hydrogen peroxide electrode or a reagent for measuring hydrogen peroxide. The reagent for measuring hydrogen peroxide is a reagent for converting such hydrogen peroxide formed, to a detectable substance. Examples of the detectable substance include a dye and a luminescent substance, and a dye is preferable. Where the detectable substance is a dye, the reagent for measuring hydrogen peroxide comprises an oxidative coloring chromogen and a peroxidative substance such as peroxidase. Examples of the oxidative coloring chromogen include an oxidative coloring chromogen described below. Where the detectable substance is a luminescent substance, the reagent for measuring hydrogen peroxide comprises a chemiluminescent substance. Examples of the chemiluminescent substance include luminol, isoluminol, lucigenin, and acridinium ester.

Where a reagent comprising an oxidative coloring chromogen and a peroxidative substance such as peroxidase is used as the reagent for measuring hydrogen peroxide, the hydrogen peroxide can be measured by forming a dye due to a reaction with the oxidative coloring chromogen in the presence of the peroxidative substance to measure the dye formed. Where a reagent for measuring hydrogen peroxide, comprising a chemiluminescent substance, is used, the hydrogen peroxide can be measured by generating photon due to a reaction with the chemiluminescent substance to measure the photon generated.

Examples of the oxidative coloring chromogen include a leuco-type chromogen and an oxidative coupling-coloring chromogen.

A leuco-type chromogen is a substance which is to be converted to a dye singly, in the presence of a peroxidative substance such as hydrogen peroxide and peroxidase. Specific examples include tetramethylbenzidine, o-phenylenediamine, 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), an N-(carboxymethylaminocarbonyl)-4,4'-bis(dimethylamino) diphenylamine sodium salt (DA-64), a 10-N-(carboxymethylaminocarbonyl)-3,7-bis(dimethylamino)-10H-phenothiazine sodium salt (DA-67), 4,4'-bis(dimethylamino) diphenylamine, and bis[3-bis(4-chlorophenyl)methyl-4-dimethylaminophenyl]amine (BCMA).

An oxidative coupling-coloring chromogen is a substance for formation of a dye by oxidative coupling of two compounds in the presence of a peroxidative substance such as hydrogen peroxide and peroxidase. Examples of a combination of such two compounds include a combination of a coupler and an aniline compound, a combination of a coupler and a phenol compound.

Examples of the coupler include 4-aminoantipyrine (4-AA) and 3-methyl-2-benzothiazolinonehydrazone.

Examples of the aniline compound include N-(3-sulfopropyl) aniline, N-ethyl-N-(2-hydroxy-3-sulfopropyl)-3-methylaniline (TOGS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, N-ethyl-N-(2-hydroxy-3-sulfopropyl)-4-fluoro-3,5-dimethoxyaniline (F-DAOS), N-[2-(succinylamino)ethyl]-2-methoxy-5-methylaniline (MASE), and N-ethyl-N-[2-(succinylamino)ethyl]-2-methoxy-5-methylaniline (Et-MASE).

Examples of the phenol compound include phenol, 4-chlorophenol, 3-methylphenol, and 3-hydroxy-2,4,6-triiodobenzoic acid (HTIB).

The concentration of the peroxidative substance in such measurement of hydrogen peroxide is not particularly limited as long as it is any concentration which enables the method for measuring LDL-C of the present invention, and is preferably 1 to 100 kU/L in the case of use of peroxidase as the peroxidative substance. The concentration of the oxidative coloring chromogen is not particularly limited as long as it is any concentration which enables the method for measuring LDL-C of the present invention, and is preferably 0.01 to 10 g/L.

Examples of the method for measuring a reduced coenzyme include a method for measuring the absorbance of a reduced coenzyme formed, and a method using a reagent for measuring a reduced coenzyme. In the method for measuring the absorbance of a reduced coenzyme, the absorbance is preferably 300 to 500 nm, more preferably 330 to 400 nm, particularly preferably around 340 nm. The reagent for measuring a reduced coenzyme is a reagent for converting a reduced coenzyme formed, to a detectable substance. Examples of the detectable substance include a dye. Where the detectable substance is a dye, examples of the reagent for measuring a reduced coenzyme include a reagent comprising diaphorase, an electronic carrier and a reductive coloring chromogen. Examples of such an electronic carrier include 1-methoxy-5-methylphenadium methylsulfate. Where such a reagent comprising diaphorase, an electronic carrier and a reductive coloring chromogen is used as the reagent for measuring a reduced coenzyme, the reduced coenzyme can be quantitatively determined by quantitatively determining a dye formed by converting the reductive coloring chromogen.

Examples of the reductive coloring chromogen include 3-(4,5-dimethyl-2-thiazolyl)-2,5-diphenyl-2H-tetrazolium bromide (MTT), a 2-(4-iodophenyl)-3-(4-nitrophenyl)-5-(2,4-disulfophenyl)-2H-tetrazolium monosodium salt (WST-1), and a 2-(4-iodophenyl)-3-(2,4-dinitrophenyl)-5-(2,4-disulfophenyl)-2H-tetrazolium monosodium salt (WST-3). The concentration of the reductive coloring chromogen is not particularly limited as long as it is any concentration which enables the method for measuring LDL-C of the present invention, and is preferably 0.01 to 10 g/L.

2. Reagent for Measuring LDL-C and Kit for Measuring LDL-C

The reagent for measuring LDL-C of the present invention is a reagent for use in the method for measuring LDL-C of the present invention. The reagent for measuring LDL-C of the present invention can be in the form of a kit suitable for conservation, distribution and use. The kit for measuring LDL-C of the present invention is a kit for use in the method for measuring LDL-C of the present invention. Example of the form of the kit for measuring LDL-C of the present invention include a two-reagent system kit and a three-reagent system kit, and a two-reagent system kit consisting of a first reagent and a second reagent is preferable.

Where LDL-C in a sample is measured by using a two-reagent system kit as the kit for measuring LDL-C of the present invention, LDL-C can be measured by first adding a sample and a first reagent into a reaction cell and reacting (primary reaction) at a certain temperature for a certain time, then adding a second reagent and furthermore reacting (secondary reaction) at a certain temperature for a certain time, and measuring a substance formed or consumed by the secondary reaction.

The reagent for measuring LDL-C of the present invention may be in a state of being freeze-dried or in a state of being dissolved in an aqueous solvent. In the case of measurement of LDL-C in a sample by use of a reagent for measuring LDL-C, which is in a state of being freeze-dried, the reagent is dissolved in an aqueous solvent in advance and used for measurement of LDL-C. Examples of the aqueous solvent include an aqueous solvent described above.

Examples of a cholesterol ester hydrolase, a cholesterol oxidase, an oxidized coenzyme, a cholesterol dehydrogenase, a surfactant having an alkylphenol structure, a POE alkyl ether, a POEPOP alkyl ether, a POEPOP copolymer, a polyoxypropylene derivative not comprising any polyoxyethylene in a molecule, reagent for measuring hydrogen peroxide, and reagent for measuring a reduced coenzyme, in the reagent for measuring LDL-C and the kit for measuring LDL-C of the present invention, include the cholesterol ester hydrolase, the cholesterol oxidase, the oxidized coenzyme, the cholesterol dehydrogenase, the surfactant having an alkylphenol structure, the POE alkyl ether, the POEPOP alkyl ether, the POEPOP copolymer, the polyoxypropylene derivative not comprising any polyoxyethylene in a molecule, the reagent for measuring hydrogen peroxide, and the reagent for measuring a reduced coenzyme, which are described above, respectively.

In a two-reagent system kit for measuring LDL-C, consisting of a first reagent and a second reagent, a surfactant having an alkylphenol structure, is comprised in neither the first reagent, nor the second reagent, and a cholesterol ester hydrolase is comprised in either the first reagent or second reagent, or in both of the first reagent and second reagents. In a two-reagent system kit for measuring LDL-C, for use in LDL-C measurement using a cholesterol ester hydrolase and a cholesterol oxidase, a cholesterol oxidase is not comprised in a first reagent, but comprised in a second reagent. In a two-reagent system kit for measuring LDL-C, for use in LDL-C measurement using a cholesterol ester hydrolase, a cholesterol dehydrogenase and an oxidized coenzyme, a cholesterol dehydrogenase is not comprised in a first reagent, but comprised in a second reagent, and an oxidized coenzyme is comprised in at least a first reagent.

While the POE alkyl ether may be comprised in either the first or second reagent, or in both of the first and the second reagent, an embodiment is preferable where the ether is comprised in the second reagent.

While the POEPOP alkyl ether may be comprised in either the first or the second reagent, or in both of the first and second reagents, an embodiment is preferable where the ether is comprised in the second reagent.

While the polyoxypropylene derivative not comprising any polyoxyethylene in a molecule may be comprised in either the first or second reagent, or in both of the first and second reagents, an embodiment is preferable where the derivative is comprised in the second reagent.

While the reagent for measuring hydrogen peroxide may be comprised in either the first or second reagent, or in both of the first and second reagents, the reagent is desirably comprised in at least the first reagent. Where the reagent for measuring hydrogen peroxide comprises an oxidative coupling chromogen, an embodiment is preferable where two compounds in the oxidative coupling chromogen, namely, a coupler and an aniline compound, or a coupler and a phenol compound are comprised in respective separate reagents. A reagent for measuring a reduced coenzyme may be comprised in either the first or second reagent, or in both of the first and second reagents, and is preferably comprised in both the first and second reagents.

Where the kit for measuring LDL-C of the present invention is a three- or more-reagent system kit, all the reagents constituting the kit do not comprise any surfactant having an alkylphenol structure.

The reagent and the kit for measuring LDL-C of the present invention may comprise, if necessary, an aqueous solvent, a stabilizer, an antiseptic, an effect avoidance agent of an interfering substance, a reaction promoter, and the like. Examples of the aqueous solvent include the above aqueous solvent. Examples of the stabilizer include ethylenediamine tetraacetic acid (EDTA), sucrose, and calcium chloride. Examples of the antiseptic include sodium azide and an antibiotic. Examples of the effect avoidance agent of an interfering substance include ascorbate oxidase for avoidance of the effect of ascorbic acid, and potassium ferrocyanide for avoidance of the effect of bilirubin. Examples of the reaction promoter include an enzyme such as colipase and phospholipase, and a salt sodium sulfate and sodium chloride.

Hereinafter, specific embodiments of the reagent for measuring LDL-C of the present invention will be described, but the reagent for measuring LDL-C of the present invention is not limited thereto.

Reagent 1

A reagent which comprises a POE alkyl ether, a POEPOP copolymer, a cholesterol ester hydrolase and a cholesterol oxidase, and which does not comprise any surfactant having an alkylphenol structure.

Reagent 2

A reagent which comprises a POE alkyl ether, a POEPOP copolymer, a cholesterol ester hydrolase, a cholesterol oxidase and a reagent for measuring hydrogen peroxide, and which does not comprise any surfactant having an alkylphenol structure.

Reagent 3

A reagent which comprises a POEPOP alkyl ether, a POEPOP copolymer, a cholesterol ester hydrolase and a cholesterol oxidase, and which does not comprise any surfactant having an alkylphenol structure.

Reagent 4

A reagent which comprises a POEPOP alkyl ether, a POEPOP copolymer, a cholesterol ester hydrolase, a cholesterol oxidase and a reagent for measuring hydrogen peroxide, and which does not comprise any surfactant having an alkylphenol structure.

Reagent 5

A reagent which comprises a POE alkyl ether, a POEPOP alkyl ether, a POEPOP copolymer, a cholesterol ester hydrolase and a cholesterol oxidase, and which does not comprise any surfactant having an alkylphenol structure.

Reagent 6

A reagent which comprises a POE alkyl ether, a POEPOP alkyl ether, a POEPOP copolymer, a cholesterol ester hydrolase, a cholesterol oxidase and a reagent for measuring hydrogen peroxide, and which does not comprise any surfactant having an alkylphenol structure.

Reagent 7

A reagent which comprises a POE alkyl ether, a POEPOP copolymer, a polyoxypropylene derivative not comprising any polyoxyethylene in a molecule, a cholesterol ester hydrolase and a cholesterol oxidase, and which does not comprise any surfactant having an alkylphenol structure.

Reagent 8

A reagent which comprises a POE alkyl ether, a POEPOP copolymer, a polyoxypropylene derivative not comprising any polyoxyethylene in a molecule, a cholesterol ester hydrolase, a cholesterol oxidase and a reagent for measuring hydrogen peroxide, and which does not comprise any surfactant having an alkylphenol structure.

Reagent 9

A reagent which comprises a POEPOP alkyl ether, a POEPOP copolymer, a polyoxypropylene derivative not comprising any polyoxyethylene in a molecule, a cholesterol ester hydrolase and a cholesterol oxidase, and which does not comprise any surfactant having an alkylphenol structure.

Reagent 10

A reagent which comprises a POEPOP alkyl ether, a POEPOP copolymer, a polyoxypropylene derivative not comprising any polyoxyethylene in a molecule, a cholesterol ester hydrolase, a cholesterol oxidase and a reagent for measuring hydrogen peroxide, and which does not comprise any surfactant having an alkylphenol structure.

Reagent 11

A reagent which comprises a POE alkyl ether, a POEPOP alkyl ether, a POEPOP copolymer, a polyoxypropylene derivative not comprising any polyoxyethylene in a molecule, cholesterol ester hydrolase and a cholesterol oxidase, and which does not comprise any surfactant having an alkylphenol structure.

Reagent 12

A reagent which comprises a POE alkyl ether, a POEPOP alkyl ether, a POEPOP copolymer, a polyoxypropylene derivative not comprising any polyoxyethylene in a molecule, a cholesterol ester hydrolase, a cholesterol oxidase and a reagent for measuring hydrogen peroxide, and which does not comprise any surfactant having an alkylphenol structure.

Reagent 13

A reagent which comprises a POE alkyl ether, a POEPOP copolymer, a cholesterol ester hydrolase, an oxidized coenzyme and a cholesterol dehydrogenase, and which does not comprise any surfactant having an alkylphenol structure.

Reagent 14

A reagent which comprises a POE alkyl ether, a POEPOP copolymer, a cholesterol ester hydrolase, an oxidized coenzyme, a cholesterol dehydrogenase and a reagent for measuring a reduced coenzyme, and which does not comprise any surfactant having an alkylphenol structure.

Reagent 15

A reagent which comprises a POEPOP alkyl ether, a POEPOP copolymer, a cholesterol ester hydrolase, an oxidized coenzyme and a cholesterol dehydrogenase, and which does not comprise any surfactant having an alkylphenol structure.

Reagent 16

A reagent which comprises a POEPOP alkyl ether, a POEPOP copolymer, a cholesterol ester hydrolase, an oxidized coenzyme, a cholesterol dehydrogenase and a reagent for measuring a reduced coenzyme, and which does not comprise any surfactant having an alkylphenol structure.

Reagent 17

A reagent which comprises a POE alkyl ether, a POEPOP alkyl ether, a POEPOP copolymer, cholesterol ester hydrolase, an oxidized coenzyme and a cholesterol dehydrogenase, and which does not comprise any surfactant having an alkylphenol structure.

Reagent 18

A reagent which comprises a POE alkyl ether, a POEPOP alkyl ether, a POEPOP copolymer, a cholesterol ester hydrolase, an oxidized coenzyme, a cholesterol dehydrogenase and a reagent for measuring a reduced coenzyme, and which does not comprise any surfactant having an alkylphenol structure.

Reagent 19

A reagent which comprises a POE alkyl ether, a POEPOP copolymer, a polyoxypropylene derivative not comprising any polyoxyethylene in a molecule, a cholesterol ester hydrolase, an oxidized coenzyme and a cholesterol dehydrogenase, and which does not comprise any surfactant having an alkylphenol structure.

Reagent 20

A reagent which comprises a POE alkyl ether, a POEPOP copolymer, a polyoxypropylene derivative not comprising any polyoxyethylene in a molecule, a cholesterol ester hydrolase, an oxidized coenzyme, a cholesterol dehydrogenase and a reagent for measuring a reduced coenzyme, and which does not comprise any surfactant having an alkylphenol structure.

Reagent 21

A reagent which comprises a POEPOP alkyl ether, a POEPOP copolymer, a polyoxypropylene derivative not comprising any polyoxyethylene in a molecule, a cholesterol ester hydrolase, an oxidized coenzyme and a cholesterol dehydrogenase, and which does not comprise any surfactant having an alkylphenol structure.

Reagent 22

A reagent which comprises a POEPOP alkyl ether, a POEPOP copolymer, a polyoxypropylene derivative not comprising any polyoxyethylene in a molecule, a cholesterol ester hydrolase, an oxidized coenzyme, a cholesterol dehydrogenase and a reagent for measuring a reduced coenzyme, and which does not comprise any surfactant having an alkylphenol structure.

Reagent 23

A reagent which comprises a POE alkyl ether, a POEPOP alkyl ether, a POEPOP copolymer, a polyoxypropylene derivative not comprising any polyoxyethylene in a molecule, a cholesterol ester hydrolase, an oxidized coenzyme and a cholesterol dehydrogenase, and which does not comprise any surfactant having an alkylphenol structure.

Reagent 24

A reagent which comprises a POE alkyl ether, a POEPOP alkyl ether, a POEPOP copolymer, a polyoxypropylene derivative not comprising any polyoxyethylene in a molecule, a cholesterol ester hydrolase, an oxidized coenzyme, a cholesterol dehydrogenase and a reagent for measuring a reduced coenzyme, and which does not comprise any surfactant having an alkylphenol structure.

The content of the cholesterol ester hydrolase in the reagent for measuring LDL-C of the present invention is not particularly limited as long as it is any content which enables the method for measuring LDL-C of the present invention, and is any content so that the concentration of the cholesterol ester hydrolase dissolved in the aqueous solvent is usually 0.001 to 800 kU/L, preferably 0.01 to 300 kU/L.

The content of the cholesterol oxidase in the reagent for measuring LDL-C of the present invention is not particularly limited as long as it is any content which enables the method for measuring LDL-C of the present invention, and is any content so that the concentration of the cholesterol oxidase dissolved in the aqueous solvent is usually 0.001 to 800 kU/L, preferably 0.01 to 300 kU/L.

The content of the cholesterol dehydrogenase in the reagent for measuring LDL-C of the present invention is not particularly limited as long as it is any content which enables the method for measuring LDL-C of the present invention, and is any content so that the concentration of the cholesterol dehydrogenase dissolved in the aqueous solvent is usually 0.001 to 800 kU/L, preferably 0.01 to 300 kU/L.

The content of the POE alkyl ether in the reagent for measuring LDL-C of the present invention is not particularly limited as long as it is any content which enables the method for measuring LDL-C of the present invention, and is any content so that the concentration of the POE alkyl ether dissolved in the aqueous solvent is usually 0.0001 to 20% (w/v), preferably 0.001 to 5% (w/v).

The content of the POEPOP alkyl ether in the reagent for measuring LDL-C of the present invention is not particularly limited as long as it is any content which enables the method for measuring LDL-C of the present invention, and is any content so that the concentration of the POEPOP alkyl ether dissolved in the aqueous solvent is usually 0.0001 to 20% (w/v), preferably 0.001 to 5% (w/v).

The content of the POEPOP copolymer in the reagent for measuring LDL-C of the present invention is not particularly limited as long as it is any content which enables the method for measuring LDL-C of the present invention, and is any content so that the concentration of the POEPOP copolymer dissolved in the aqueous solvent is usually 0.0001 to 20% (w/v), preferably 0.001 to 5% (w/v).

The content of the polyoxypropylene derivative not comprising any polyoxyethylene in a molecule, in the reagent for measuring LDL-C of the present invention, is not particularly limited as long as it is any content which enables the method for measuring LDL-C of the present invention, and is any content so that the concentration of the polyoxypropylene derivative dissolved in the aqueous solvent is usually 0.0001 to 5% (w/v), preferably 0.001 to 1% (w/v).

Hereinafter, specific embodiments of the kit for measuring LDL-C of the present invention will be described, but the kit for measuring LDL-C of the present invention is not limited thereto.

Kit 1
First Reagent
 A POE alkyl ether and a POEPOP copolymer
Second Reagent
 A cholesterol ester hydrolase and a cholesterol oxidase
It is noted that neither the first reagent nor the second reagent comprises a surfactant having an alkylphenol structure.

Kit 2
First Reagent
 A POE alkyl ether, a POEPOP copolymer and a reagent for measuring hydrogen peroxide
Second Reagent
 A cholesterol ester hydrolase, a cholesterol oxidase and a reagent for measuring hydrogen peroxide
It is noted that neither the first reagent nor the second reagent comprises a surfactant having an alkylphenol structure.

Kit 3
First Reagent
 A reagent for measuring hydrogen peroxide
Second Reagent
 A POE alkyl ether, a POEPOP copolymer, a cholesterol ester hydrolase, a cholesterol oxidase and a reagent for measuring hydrogen peroxide
It is noted that neither the first reagent nor the second reagent comprises a surfactant having an alkylphenol structure.

Kit 4
First Reagent
 A POEPOP alkyl ether and a POEPOP copolymer
Second Reagent
 A cholesterol ester hydrolase and a cholesterol oxidase
It is noted that neither the first reagent nor the second reagent comprises a surfactant having an alkylphenol structure.

Kit 5
First Reagent
 A POEPOP alkyl ether, a POEPOP copolymer and a reagent for measuring hydrogen peroxide
Second Reagent
 A cholesterol ester hydrolase, a cholesterol oxidase and a reagent for measuring hydrogen peroxide
It is noted that neither the first reagent nor the second reagent comprises a surfactant having an alkylphenol structure.

Kit 6
First Reagent
 A reagent for measuring hydrogen peroxide
Second Reagent
 A POEPOP alkyl ether, a POEPOP copolymer, a cholesterol ester hydrolase, a cholesterol oxidase and a reagent for measuring hydrogen peroxide
It is noted that neither the first reagent nor the second reagent comprises a surfactant having an alkylphenol structure.

Kit 7
First Reagent
 A POE alkyl ether, POEPOP alkyl ether and a POEPOP copolymer
Second Reagent
 A Cholesterol Ester Hydrolase and a Cholesterol Oxidase
It is noted that neither the first reagent nor the second reagent comprises a surfactant having an alkylphenol structure.

Kit 8
First Reagent
 A POE alkyl ether, a POEPOP alkyl ether, a POEPOP copolymer and a reagent for measuring hydrogen peroxide
Second Reagent
 A Cholesterol Ester Hydrolase, a Cholesterol Oxidase and a Reagent for Measuring Hydrogen Peroxide
It is noted that neither the first reagent nor the second reagent comprises a surfactant having an alkylphenol structure.

Kit 9
First Reagent
 A reagent for measuring hydrogen peroxide
Second Reagent
 A POE alkyl ether, a POEPOP alkyl ether, a POEPOP-copolymer, a cholesterol ester hydrolase, a cholesterol oxidase and a reagent for measuring hydrogen peroxide It is noted that neither the first reagent nor the second reagent comprises a surfactant having an alkylphenol structure.

Kit 10
First Reagent
   A POE alkyl ether and a POEPOP copolymer
Second Reagent
   A polyoxypropylene derivative not comprising any polyoxyethylene in a molecule, a cholesterol ester hydrolase and a cholesterol oxidase
It is noted that neither the first reagent nor the second reagent comprises a surfactant having an alkylphenol structure.

Kit 11
First Reagent
   A POE alkyl ether, a POEPOP copolymer and a reagent for measuring hydrogen peroxide
Second Reagent
   A polyoxypropylene derivative not comprising any polyoxyethylene in a molecule, a cholesterol ester hydrolase, a cholesterol oxidase and a reagent for measuring hydrogen peroxide
It is noted that neither the first reagent nor the second reagent comprises a surfactant having an alkylphenol structure.

Kit 12
First Reagent
   A reagent for measuring hydrogen peroxide
Second Reagent
   A POE alkyl ether, a POEPOP copolymer, a polyoxypropylene derivative not comprising any polyoxyethylene in a molecule, a cholesterol ester hydrolase, a cholesterol oxidase and a reagent for measuring hydrogen peroxide
It is noted that neither the first reagent nor the second reagent comprises a surfactant having an alkylphenol structure.

Kit 13
First Reagent
   A POEPOP alkyl ether and a POEPOP copolymer
Second Reagent
   A polyoxypropylene derivative not comprising any polyoxyethylene in a molecule, a cholesterol ester hydrolase and a cholesterol oxidase
It is noted that neither the first reagent nor the second reagent comprises a surfactant having an alkylphenol structure.

Kit 14
First Reagent
   A POEPOP alkyl ether, a POEPOP copolymer and a reagent for measuring hydrogen peroxide
Second Reagent
   A polyoxypropylene derivative not comprising any polyoxyethylene in a molecule, a cholesterol ester hydrolase, a cholesterol oxidase and a reagent for measuring hydrogen peroxide
It is noted that neither the first reagent nor the second reagent comprises a surfactant having an alkylphenol structure.

Kit 15
First Reagent
   A reagent for measuring hydrogen peroxide
Second Reagent
   A POEPOP alkyl ether, a POEPOP copolymer, a polyoxypropylene derivative not comprising any polyoxyethylene in a molecule, a cholesterol ester hydrolase, a cholesterol oxidase and a reagent for measuring hydrogen peroxide
It is noted that neither the first reagent nor the second reagent comprises a surfactant having an alkylphenol structure.

Kit 16
First Reagent
   A POE alkyl ether, a POEPOP alkyl ether and a POEPOP copolymer
Second Reagent
   A polyoxypropylene derivative not comprising any polyoxyethylene in a molecule, a cholesterol ester hydrolase and a cholesterol oxidase
It is noted that neither the first reagent nor the second reagent comprises a surfactant having an alkylphenol structure.

Kit 17
First Reagent
   A POE alkyl ether, a POEPOP alkyl ether, a POEPOP copolymer and a reagent for measuring hydrogen peroxide
Second Reagent
   A polyoxypropylene derivative not comprising any polyoxyethylene in a molecule, a cholesterol ester hydrolase, a cholesterol oxidase and a reagent for measuring hydrogen peroxide
It is noted that neither the first reagent nor the second reagent comprises a surfactant having an alkylphenol structure.

Kit 18
First Reagent
   A reagent for measuring hydrogen peroxide
Second Reagent
   A POE alkyl ether, a POEPOP alkyl ether, a POEPOP copolymer, a polyoxypropylene derivative not comprising any polyoxyethylene in a molecule, a cholesterol ester hydrolase, a cholesterol oxidase and a reagent for measuring hydrogen peroxide
It is noted that neither the first reagent nor the second reagent comprises a surfactant having an alkylphenol structure.

Kit 19
First Reagent
   A POE alkyl ether, a POEPOP copolymer and an oxidized coenzyme
Second Reagent
   A cholesterol ester hydrolase and a cholesterol dehydrogenase
It is noted that neither the first reagent nor the second reagent comprises a surfactant having an alkylphenol structure.

Kit 20
First Reagent
   A POE alkyl ether, a POEPOP copolymer, an oxidized coenzyme and a reagent for measuring a reduced coenzyme
Second Reagent
   A cholesterol ester hydrolase, a cholesterol dehydrogenase and a reagent for measuring a reduced coenzyme
It is noted that neither the first reagent nor the second reagent comprises a surfactant having an alkylphenol structure.

Kit 21
First Reagent
   An oxidized coenzyme
Second Reagent
   A POE alkyl ether, a POEPOP copolymer, a cholesterol ester hydrolase and a cholesterol dehydrogenase
It is noted that neither the first reagent nor the second reagent comprises a surfactant having an alkylphenol structure.

Kit 22
First Reagent
   An oxidized coenzyme and a reagent for measuring a reduced coenzyme
Second Reagent
   A POE alkyl ether, a POEPOP copolymer, a cholesterol ester hydrolase, a cholesterol dehydrogenase and a reagent for measuring a reduced coenzyme It is noted that neither the first reagent nor the second reagent comprises a surfactant having an alkylphenol structure.
Kit 23
First Reagent
A POEPOP alkyl ether, a POEPOP copolymer and an oxidized coenzyme
Second Reagent
A Cholesterol ester hydrolase and a cholesterol dehydrogenase
It is noted that neither the first reagent nor the second reagent comprises a surfactant having an alkylphenol structure.
Kit 24
First Reagent
A POEPOP alkyl ether, a POEPOP copolymer, an oxidized coenzyme and a reagent for measuring a reduced coenzyme
Second Reagent
A Cholesterol ester hydrolase, a cholesterol dehydrogenase and a reagent for measuring a reduced coenzyme
It is noted that neither the first reagent nor the second reagent comprises a surfactant having an alkylphenol structure.
Kit 25
First Reagent
An oxidized coenzyme
Second Reagent
A POEPOP alkyl ether, a POEPOP copolymer, a cholesterol ester hydrolase and a cholesterol dehydrogenase
It is noted that neither the first reagent nor the second reagent comprises a surfactant having an alkylphenol structure.
Kit 26
First Reagent
An oxidized coenzyme and a reagent for measuring a reduced coenzyme
Second Reagent
A POEPOP alkyl ether, a POEPOP copolymer, a cholesterol ester hydrolase, a cholesterol dehydrogenase and a reagent for measuring a reduced coenzyme
It is noted that neither the first reagent nor the second reagent comprises a surfactant having an alkylphenol structure.
Kit 27
First Reagent
A POE alkyl ether, POEPOP alkyl ether, a POEPOP copolymer and an oxidized coenzyme
Second Reagent
A Cholesterol ester hydrolase and a cholesterol dehydrogenase
It is noted that neither the first reagent nor the second reagent comprises a surfactant having an alkylphenol structure.
Kit 28
First Reagent
A POE alkyl ether, a POEPOP alkyl ether, a POEPOP copolymer, an oxidized coenzyme and a reagent for measuring a reduced coenzyme
Second Reagent
A cholesterol ester hydrolase, a cholesterol dehydrogenase and a reagent for measuring a reduced coenzyme It is noted that neither the first reagent nor the second reagent comprises a surfactant having an alkylphenol structure.
Kit 29
First Reagent
An oxidized coenzyme
Second Reagent
A POE alkyl ether, a POEPOP alkyl ether, a POEPOP copolymer, a cholesterol ester hydrolase and a cholesterol dehydrogenase
It is noted that neither the first reagent nor the second reagent comprises a surfactant having an alkylphenol structure.
Kit 30
First Reagent
An oxidized coenzyme and a reagent for measuring a reduced coenzyme
Second Reagent
A POE alkyl ether, a POEPOP alkyl ether, a POEPOP copolymer, a cholesterol ester hydrolase, a cholesterol dehydrogenase and a reagent for measuring a reduced coenzyme
It is noted that neither the first reagent nor the second reagent comprises a surfactant having an alkylphenol structure.
Kit 31
First Reagent
POE alkyl ether, a POEPOP copolymer and an oxidized coenzyme
Second Reagent
A polyoxypropylene derivative not comprising any polyoxyethylene in a molecule, a cholesterol ester hydrolase and a cholesterol dehydrogenase
It is noted that neither the first reagent nor the second reagent comprises a surfactant having an alkylphenol structure.
Kit 32
First Reagent
A POE alkyl ether, a POEPOP copolymer, an oxidized coenzyme and a reagent for measuring a reduced coenzyme
Second Reagent
A polyoxypropylene derivative not comprising any polyoxyethylene in a molecule, a cholesterol ester hydrolase, a cholesterol dehydrogenase and a reagent for measuring a reduced coenzyme
It is noted that neither the first reagent nor the second reagent comprises a surfactant having an alkylphenol structure.
Kit 33
First Reagent
An oxidized coenzyme
Second Reagent
A POE alkyl ether, a POEPOP copolymer, a polyoxypropylene derivative not comprising any polyoxyethylene in a molecule, a cholesterol ester hydrolase and a cholesterol dehydrogenase
It is noted that neither the first reagent nor the second reagent comprises a surfactant having an alkylphenol structure.
Kit 34
First Reagent
An oxidized coenzyme and a reagent for measuring a reduced coenzyme
Second Reagent
A POE alkyl ether, a POEPOP copolymer, a polyoxypropylene derivative not comprising any polyoxyethylene in a molecule, a cholesterol ester hydrolase, cholesterol dehydrogenase and a reagent for measuring a reduced coenzyme
It is noted that neither the first reagent nor the second reagent comprises a surfactant having an alkylphenol structure.
Kit 35
First Reagent
A POEPOP alkyl ether, a POEPOP copolymer and an oxidized coenzyme
Second Reagent
A polyoxypropylene derivative not comprising any polyoxyethylene in a molecule, a cholesterol ester hydrolase and a cholesterol dehydrogenase
It is noted that neither the first reagent nor the second reagent comprises a surfactant having an alkylphenol structure.
Kit 36
First Reagent
A POEPOP alkyl ether, a POEPOP copolymer, an oxidized coenzyme and a reagent for measuring a reduced coenzyme Second Reagent A polyoxypropylene derivative not comprising any polyoxyethylene in a molecule, a cholesterol ester hydrolase, a cholesterol dehydrogenase and a reagent for measuring a reduced coenzyme It is noted that neither the first reagent nor the second reagent comprises a surfactant having an alkylphenol structure.

Kit 37
First Reagent

An oxidized coenzyme

Second Reagent

A POEPOP alkyl ether, a POEPOP copolymer, a polyoxypropylene derivative not comprising any polyoxyethylene in a molecule, a cholesterol ester hydrolase and a cholesterol dehydrogenase It is noted that neither the first reagent nor the second reagent comprises a surfactant having an alkylphenol structure.

Kit 38
First Reagent

An oxidized coenzyme and a reagent for measuring a reduced coenzyme

Second Reagent

A POEPOP alkyl ether, a POEPOP copolymer, a polyoxypropylene derivative not comprising any polyoxyethylene in a molecule, a cholesterol ester hydrolase, a cholesterol dehydrogenase and a reagent for measuring a reduced coenzyme It is noted that neither the first reagent nor the second reagent comprises a surfactant having an alkylphenol structure.

Kit 39
First Reagent

A POE alkyl ether, a POEPOP alkyl ether, a POEPOP copolymer and an oxidized coenzyme Second Reagent A polyoxypropylene derivative not comprising any polyoxyethylene in a molecule, a cholesterol ester hydrolase and a cholesterol dehydrogenase It is noted that neither the first reagent nor the second reagent comprises a surfactant having an alkylphenol structure.

Kit 40
First Reagent

A POE alkyl ether, a POEPOP alkyl ether, a POEPOP copolymer, an oxidized coenzyme and a reagent for measuring a reduced coenzyme Second Reagent A polyoxypropylene derivative not comprising any polyoxyethylene in a molecule, cholesterol ester hydrolase, a cholesterol dehydrogenase and a reagent for measuring a reduced coenzyme It is noted that neither the first reagent nor the second reagent comprises a surfactant having an alkylphenol structure.

Kit 41
First Reagent

An oxidized coenzyme

Second Reagent

A POE alkyl ether, a POEPOP alkyl ether, a POEPOP copolymer, a polyoxypropylene derivative not comprising any polyoxyethylene in a molecule, a cholesterol ester hydrolase and a cholesterol dehydrogenase It is noted that neither the first reagent nor the second reagent comprises a surfactant having an alkylphenol structure.

Kit 42
First Reagent

An oxidized coenzyme and a reagent for measuring a reduced coenzyme

Second Reagent

A POE alkyl ether, a POEPOP alkyl ether, a POEPOP copolymer, a polyoxypropylene derivative not comprising any polyoxyethylene in a molecule, a cholesterol ester hydrolase, a cholesterol dehydrogenase and a reagent for measuring a reduced coenzyme It is noted that neither the first reagent nor the second reagent comprises a surfactant having an alkylphenol structure.

The content of the cholesterol ester hydrolase in the first reagent constituting the kit for measuring LDL-C of the present invention is not particularly limited as long as it is any content which enables the method for measuring LDL-C of the present invention, and is any content so that the concentration of the cholesterol ester hydrolase dissolved in the aqueous solvent is usually 0.002 to 1600 kU/L, preferably 0.02 to 600 kU/L.

The content of the cholesterol ester hydrolase in the second reagent constituting the kit for measuring LDL-C of the present invention is not particularly limited as long as it is any content which enables the method for measuring LDL-C of the present invention, and any content so that the concentration of the cholesterol ester hydrolase dissolved in the aqueous solvent is usually 0.004 to 3200 kU/L, preferably 0.04 to 1200 kU/L.

The content of the cholesterol oxidase in the second reagent constituting the kit for measuring LDL-C of the present invention is not particularly limited as long as it is any content which enables the method for measuring LDL-C of the present invention, and is any content so that the concentration of the cholesterol oxidase dissolved in the aqueous solvent is usually 0.004 to 3200 kU/L, preferably 0.04 to 1200 kU/L.

The content of the cholesterol dehydrogenase in the second reagent constituting the kit for measuring LDL-C of the present invention is not particularly limited as long as it is any content which enables the method for measuring LDL-C of the present invention, and is any content so that the concentration of the cholesterol dehydrogenase dissolved in the aqueous solvent is usually 0.004 to 3200 kU/L, preferably 0.04 to 1200 kU/L.

The content of the POE alkyl ether in the first reagent constituting the kit for measuring LDL-C of the present invention is not particularly limited as long as it is any content which enables the method for measuring LDL-C of the present invention, and is any content so that the concentration of the POE alkyl ether dissolved in the aqueous solvent is usually 0.0002 to 40% (w/v), preferably 0.002 to 10% (w/v).

The content of the POE alkyl ether in the second reagent constituting the kit for measuring LDL-C of the present invention is not particularly limited as long as it is any content which enables the method for measuring LDL-C of the present invention, and is any content so that the concentration of the POE alkyl ether dissolved in the aqueous solvent is usually 0.0004 to 40% (w/v), preferably 0.004 to 20% (w/v).

The content of the POEPOP alkyl ether in the first reagent constituting the kit for measuring LDL-C of the present invention is not particularly limited as long as it is any content which enables the method for measuring LDL-C of the present invention, and is any content so that the concentration of the POEPOP alkyl ether dissolved in the aqueous solvent is usually 0.0002 to 40% (w/v), preferably 0.002 to 10% (w/v).

The content of the POEPOP alkyl ether in the second reagent constituting the kit for measuring LDL-C of the present invention is not particularly limited as long as it is any content which enables the method for measuring LDL-C of the present invention, and is any content so that the concentration of the POEPOP alkyl ether dissolved in the aqueous solvent is usually 0.0004 to 40% (w/v), preferably 0.004 to 20% (w/v).

The content of the POEPOP copolymer in the first reagent constituting the kit for measuring LDL-C of the present invention is not particularly limited as long as it is any content which enables the method for measuring LDL-C of the present invention, and is any content so that the concentration of the POEPOP copolymer dissolved in the aqueous solvent is usually 0.0002 to 40% (w/v), preferably 0.002 to 10% (w/v).

The content of the POEPOP copolymer in the second reagent constituting the kit for measuring LDL-C of the present invention is not particularly limited as long as it is any content which enables the method for measuring LDL-C of the present invention, and is any content so that the concentration of the POEPOP copolymer dissolved in the aqueous solvent is usually 0.0004 to 40% (w/v), preferably 0.004 to 20% (w/v).

The content of the polyoxypropylene derivative not comprising any polyoxyethylene in a molecule, in the first reagent constituting the kit for measuring LDL-C of the present invention, is not particularly limited as long as it is any content which enables the method for measuring LDL-C of the present invention, and is any content so that the concentration of the polyoxypropylene derivative dissolved in the aqueous solvent is usually 0.0002 to 10% (w/v), preferably 0.002 to 2% (w/v).

The content of the polyoxypropylene derivative not comprising any polyoxyethylene in a molecule, in the second reagent constituting the kit for measuring LDL-C of the present invention, is not particularly limited as long as it is any content which enables the method for measuring LDL-C of the present invention, and is any content so that the concentration of the polyoxypropylene derivative dissolved in the aqueous solvent is usually 0.0004 to 20% (w/v), preferably 0.004 to 4% (w/v).

EXAMPLES

Hereinafter, the present invention will be described in more detail with reference to Examples, but such Examples do not limit the scope of the present invention at all. Reagents and enzymes from manufacturers described below were used in the present Examples and Comparative Examples.

PIPES (manufactured by Dojindo Laboratories), EMSE (manufactured by Daito Chemix Co., Ltd.), ascorbate oxidase (manufactured by Asahi Kasei Pharma Corporation), 4-AA (manufactured by Actec), calcium chloride (manufactured by Wako Pure Chemical Industries, Ltd.), potassium ferrocyanide (manufactured by Kanto Kagaku), LPL-311 (cholesterol ester hydrolase; manufactured by Toyobo Co., Ltd.), CHO-CE (cholesterol oxidase; manufactured by Kikkoman Corporation), peroxidase (manufactured by Toyobo Co., Ltd.), and Pluronic L-121 (POEPOP copolymer; manufactured by ADEKA Corporation)

Safetycut ID-1087 (POE isodecyl ether; manufactured by Aoki Oil Industrial Co., Ltd.), Finesurf TD-200 (POE tridecyl ether; manufactured by Aoki Oil Industrial Co., Ltd.), Wondersurf ID-70 (POEPOP isodecyl ether; manufactured by Aoki Oil Industrial Co., Ltd.), Wondersurf ID-90 (POEPOP isodecyl ether; manufactured by Aoki Oil Industrial Co., Ltd.), and Wondersurf S-1400 (POEPOP tridecyl ether; manufactured by Aoki Oil Industrial Co., Ltd.)

Rheodol TW-L120 (polyoxyethylene sorbitan monolaurate; manufactured by Kao Corporation), Emanon 1112 (polyethylene glycol monolaurate; manufactured by Kao Corporation), Nymeen L-207 (polyoxyethylene laurylamine; manufactured by NOF Corporation), Unigly MK-278 (polyoxyethylene coconut oil fatty acid glyceryl; manufactured by NOF Corporation), and Uniox HC-100 (polyoxyethylene hardened castor oil; manufactured by NOF Corporation)

Uniol D-1200 (polypropylene glycol; manufactured by NOF Corporation), Uniol D-2000 (polypropylene glycol; manufactured by NOF Corporation), polypropylene glycol diol type 3,000 (polypropylene glycol; manufactured by Wako Pure Chemical Industries, Ltd.), Uniol TG-3000 (polyoxypropylene glyceryl ether; manufactured by NOF Corporation), and PEG #2000 (polyethylene glycol; manufactured by NOF Corporation)

Normal saline (manufactured by Otsuka Pharmaceutical Factory, Inc.), 10% intralipos injection (purified soybean oil; manufactured by Otsuka Pharmaceutical Factory, Inc.), Determiner L TCII (kit for measuring cholesterol; manufactured by Kyowa Medex Co., Ltd.), MetaboLead LDL-C (kit for measuring LDL-C; manufactured by Kyowa Medex Co., Ltd.), Determiner for measuring standard serum lipid (standard preparation to be used in combination with Determiner L TCII; manufactured by Kyowa Medex Co., Ltd., hereinafter, abbreviated as cholesterol standard preparation), and MetaboLead for measuring standard serum HDL/LDL-C (standard preparation to be used in combination with MetaboLead LDL-C; manufactured by Kyowa Medex Co., Ltd., hereinafter, abbreviated as LDL-C standard preparation)

Reference Example 1

Preparation of Lipoprotein Fraction and Determination of Concentration of Cholesterol (1) Preparation of Lipoprotein Fraction Whole blood collected from a healthy individual belonging to Kyowa Medex Co., Ltd. was centrifuged at 3,000 rpm and 25° C. for 20 minutes, thereby preparing a human serum. Then, VLDL (specific gravity: 1.006 or less), LDL (specific gravity: 1.006 to 1.063), and HDL (specific gravity: 1.063 or more) were each separated from the human serum according to an ultracentrifugation step described in "Novel Biochemistry Experiment Lectures, Vol. 4, Lipid I, Triglyceride and Lipoprotein" (Tokyo Kagaku Dojin-sha, ISBN: 4-8079-1080-9), thereby preparing each lipoprotein fraction.

(2) Creation of Calibration Curve for Determination of Concentration of Cholesterol Determiner L TCII was used for a kit for measuring cholesterol and a cholesterol standard preparation where the concentration of cholesterol was determined was used for a sample, and the absorbance for the cholesterol standard preparation was measured according to the following procedure. The standard preparation (2 µL) and a first reagent (150 µL) of Determiner L TCII were added to a reaction cell and allowed to react at 37° C. for 5 minutes, and the absorbance (E1) of such a reaction liquid was measured at a main wavelength of 600 nm and a sub-wavelength of 800 nm. Then, a second reagent (50 µL) of Determiner L TCII was added to the reaction liquid and further allowed to react at 37° C. for 5 minutes, and the absorbance (E2) of the reaction liquid was measured at a main wavelength of 600 nm and a sub-wavelength of 800 nm. E1 was subtracted from E2, and the difference in absorbance ΔE standard preparation was calculated.

The difference in absorbance ΔE blank was calculated by the same method except that normal saline was used instead of the standard preparation.

A calibration curve showing a relationship between the concentration of cholesterol (mg/dL) and the absorbance was created from the difference in absorbance ΔE standard preparation for the standard preparation and the difference in absorbance ΔE blank for normal saline.

(3) Determination of Concentration of Cholesterol in Each Lipoprotein Fraction

Determiner L TCII was used for a kit for measuring cholesterol and each lipoprotein fraction prepared in (1) was used for a sample, and the difference in absorbance for the lipoprotein fraction was calculated according to the same procedure as in (2). The concentration of cholesterol (mg/dL) in the lipoprotein fraction was determined from the difference in absorbance, calculated, and the calibration curve in (2).

Example 1

Each kit for measuring LDL-C(kits 1A to 1E) consisting of the following first reagent and second reagent was prepared.

| First reagent | |
|---|---|
| PIPES (pH 7.0) | 50 mmol/L |
| EMSE | 0.3 g/L |
| Ascorbate oxidase | 4 kU/L |
| Second reagent | |
| PIPES (pH 7.0) | 50 mmol/L |
| 4-AA | 0.5 g/L |
| Calcium chloride | 0.1 g/L |
| Potassium ferrocyanide | 0.02 g/L |
| LPL-311 | 3 kU/L |
| CHO-CE | 2 kU/L |
| Peroxidase | 20 kU/L |
| Pluronic L-121 | 7 g/L |
| Surfactants A to E (see Table 1) | |

Comparative Example 1

Each kit for measuring LDL-C(kits 1a to 1e) consisting of the following first reagent and second reagent was prepared.

| First reagent | |
|---|---|
| PIPES (pH 7.0) | 50 mmol/L |
| EMSE | 0.3 g/L |
| Ascorbate oxidase | 4 kU/L |
| Second reagent | |
| PIPES (pH 7.0) | 50 mmol/L |
| 4-AA | 0.5 g/L |
| Calcium chloride | 0.1 g/L |
| Potassium ferrocyanide | 0.02 g/L |
| LPL-311 | 3 kU/L |

-continued

| | |
|---|---|
| CHO-CE | 2 kU/L |
| Peroxidase | 20 kU/L |
| Pluronic L-121 | 7 g/L |
| Surfactants a to e (see Table 1) | |

Example 2

Kit 1A of Example 1 was used for a kit for measuring LDL-C and each lipoprotein fraction prepared in (1) of Reference Example 1 was used for a sample, and the reaction rate of cholesterol in the lipoprotein fraction was determined according to the following procedure. Kit 1A of Example 1 and MetaboLead LDL-C were used for a kit for measuring LDL-C and twenty human serums prepared in (4) described below were used for a sample, and the correlation between a measurement method using kit 1A of Example 1 and a measurement method using MetaboLead LDL-C was verified to determine the correlation coefficient, according to the following procedure.

(1) Creation of Calibration Curve for Determination of Concentration of LDL-C

Kit 1A of Example 1 was used for a kit for measuring LDL-C and a LDL-C standard preparation where the concentration of LDL-C was determined was used for a sample, and the absorbance for the LDL-C standard preparation was measured according to the following procedure. The standard preparation (2.5 μL) and a first reagent (150 μL) of kit 1A of Example 1 were added to a reaction cell and allowed to react at 37° C. for 5 minutes, and the absorbance (E1) of such a reaction liquid was at a main wavelength of 600 nm and a sub-wavelength of 700 nm. Then, a second reagent (50 μL) of kit 1A of Example 1 was added to the reaction liquid and further allowed to react at 37° C. for 5 minutes, and the absorbance (E2) of the reaction liquid was measured at a main wavelength of 600 nm and a sub-wavelength of 700 nm. E1 was subtracted from E2, and the difference in absorbance $\Delta E_{standard\ preparation}$ was calculated.

The difference in absorbance ΔE blank was calculated by the same method except that normal saline was used instead of the standard preparation.

A calibration curve showing a relationship between the concentration of LDL-C(mg/dL) and the absorbance was created from the difference in absorbance $\Delta E_{standard\ preparation}$ for the standard preparation and the difference in absorbance ΔE blank for normal saline.

(2) Determination of Concentration of Cholesterol in Each Lipoprotein Fraction

Kit 1A of Example 1 was used and each lipoprotein fraction prepared in (1) of Reference Example 1 was used for a sample, and the difference in absorbance for cholesterol in the lipoprotein fraction was calculated according to the same procedure as in (1). The concentration of cholesterol (mg/dL) in the lipoprotein fraction was determined from the difference in absorbance, calculated, and the calibration curve in (1).

(3) Determination of Reaction Rate of Cholesterol in Each Lipoprotein Fraction

The reaction rate of cholesterol in each lipoprotein fraction in kit 1A of Example 1 was determined from the concentration of cholesterol in each lipoprotein fraction, determined in (3) of Reference Example 1, and the concentration of cholesterol in each lipoprotein fraction, determined in the aforementioned (2), according to the following equation (I).

[Equation 1]

$$\text{Reaction rate (\%) of cholesterol in each lipoprotein fraction} = \frac{\text{Concentration of cholesterol in each lipoprotein fraction, determined in (2)}}{\text{Concentration of cholesterol in each lipoprotein fraction}} \times 100 \quad (I)$$

The reaction rate of cholesterol in each lipoprotein fraction, determined, is represented by "−" in the case of a reaction rate of 0% or more and less than 10%, "±" in the case of a reaction rate of 10% or more and less than 20%, "+" in the case of a reaction rate of 20% or more and less than 40%, or "++" in the case of a reaction rate of 40% or more, and the results are shown in Table 1.

(4) Determination of Concentration of LDL-C in Human Serum

Whole blood collected from a healthy individual belonging to Kyowa Medex Co., Ltd. was centrifuged at 3,000 rpm and 25° C. for 20 minutes, thereby preparing twenty human serum samples. Then, kit 1A of Example 1 and MetaboLead LDL-C were used for a kit for measuring LDL-C and the twenty human serums were used for a sample, and the difference in absorbance for each of the human serums was calculated according to the same procedure as in (1). The concentration of LDL-C(mg/dL) in the human serum was determined from the difference in absorbance, calculated, and the calibration curve in (1).

(5) Determination of Correlation Coefficient Between Measurement Method Using Measurement Kit of Present Invention and Measurement Method Using MetaboLead LDL-C The correlation between a measurement method using kit 1A of Example 1 and a measurement method using MetaboLead LDL-C was verified to determine the correlation coefficient, from the concentration of LDL-C(mg/dL) in each human serum, determined according to (4) with kit 1A of Example 1 for a kit for measuring LDL-C, and the concentration of LDL-C (mg/dL) in each human serum, determined according to (4) with MetaboLead LDL-C for a kit for measuring LDL-C. The results are shown in Table 1.

Example 3

The same procedure as in Example 2 except that each kit of kits 1B, 1C, 1D and 1E of Example 1, instead of kit 1A of Example 1, was used for a kit for measuring LDL-C was performed to determine the reaction rate of cholesterol in each lipoprotein fraction in each of the kits, and the correlation coefficient between a measurement method using each of the kits and the measurement method using MetaboLead LDL-C. The results are shown in Table 1.

Comparative Example 2

The same procedure as in Example 2 except that each kit of kits 1a, 1b, 1c, 1d and 1e of Comparative Example 1, instead of kit 1A of Example 1, was used for a kit for measuring LDL-C was performed to determine the reaction rate of cholesterol in each lipoprotein fraction in each of the kits, and the correlation coefficient between a measurement method using each of the kits and the measurement method using MetaboLead LDL-C. The results are shown in Table 1.

TABLE 1

| Kit | Nonionic surfactant Product name (concentration) | | Structure | Reaction rate of cholesterol in lipoprotein fraction VLDL fraction | LDL fraction | HDL fraction | Correlation coefficient |
|---|---|---|---|---|---|---|---|
| 1A | A | Safetycut ID-1087 (6 g/L) | POE isodecyl ether | ± | ++ | − | 0.987 |
| 1B | B | Finesurf TD-200 (6 g/L) | POE tridecyl ether | ± | + | − | 0.961 |
| 1C | C | Wondersurf ID-70 (5 g/L) | POEPOP isodecyl ether | + | ++ | − | 0.980 |
| 1D | D | Wondersurf ID-90 (5 g/L) | POEPOP isodecyl ether | ± | ++ | − | 0.985 |
| 1E | E | Wondersurf S-1400 (4 g/L) | POEPOP tridecyl ether | ± | ++ | − | 0.992 |
| 1a | a | Rheodol TW-L120 (4 g/L) | Polyoxyethylene sorbitan monolaurate | + | − | ± | 0.103 |
| 1b | b | Emanon 1112 (4 g/L) | Polyethylene glycol monolaurate | ++ | ± | + | 0.599 |
| 1c | c | Nymeen L-207 (4 g/L) | Polyoxyethylene laurylamine | − | − | − | 0.441 |
| 1d | d | Unigly MK-278 (4 g/L) | Polyoxyethylene coconut oil fatty acid glyceryl | ++ | + | ++ | 0.543 |
| 1e | e | Uniox HC-100 (4 g/L) | Polyoxyethylene hardened castor oil | ++ | + | + | 0.494 |

As described in (1) of Reference Example 1, each lipoprotein fraction used for measurement was prepared by separating VLDL, LDL and HDL according to an ultracentrifugation method. Accordingly, it is meant that, as a kit for measuring LDL-C is lower in the reaction rate of cholesterol in a VLDL fraction and the reaction rate of cholesterol in a HDL fraction, and higher in the reaction rate of cholesterol in a LDL fraction, LDL-C in a sample can be more accurately measured. As clear from Table 1, it was found that measurement using each kit of kits 1A to 1E of Example 1 exhibited low reaction rates in a VLDL fraction and a HDL fraction and a high reaction rate in a LDL fraction as compared with measurement using each kit of kits 1a to 1e of Comparative Example 1. Accordingly, it has been revealed that LDL-C in a sample can be accurately measured by the method for measuring LDL-C of the present invention by use of the kit for measuring LDL-C of the present invention, comprising one or more surfactants selected from the group consisting of POE alkyl ether and POEPOP alkyl ether, and a POEPOP copolymer.

As clear from Table 1, the correlation coefficient between a measurement method using each kit of kits 1A to 1E of Example 1 and the measurement method using MetaboLead LDL-C was 0.95 or more, and favorable correlation between both such measurements was confirmed. On the other hand, there was not confirmed any favorable correlation between a measurement method using each kit of kits 1a to 1e of Comparative Example 1 and the measurement method using MetaboLead LDL-C. Accordingly, it has been revealed that LDL-C in a sample can be accurately measured by the method for measuring LDL-C of the present invention by use of the kit for measuring LDL-C of the present invention, comprising one or more surfactants selected from the group consisting of POE alkyl ether and POEPOP alkyl ether, and a POEPOP copolymer.

Example 4

Whole blood collected from a healthy individual belonging to Kyowa Medex Co., Ltd. was centrifuged at 3,000 rpm and 25° C. for 20 minutes, thereby preparing five human serum samples. Then, kit 1E of Example 1 and MetaboLead LDL-C were used for a kit for measuring LDL-C and the five human serums were used for a sample, and the concentration of LDL-C(mg/dL) in each of the human serum was determined according to the same procedures as in (1) and (2) of Example 2. The results are shown in Table 2.

TABLE 2

| | Measurement value [mg/dL] | |
|---|---|---|
| Sample | Kit 1E | MetaboLead LDL-C |
| Serum 1 | 64 | 69 |
| Serum 2 | 96 | 96 |
| Serum 3 | 105 | 108 |
| Serum 4 | 129 | 128 |
| Serum 5 | 144 | 152 |

As clear from Table 2, the concentration of LDL-C (mg/dL) determined in measurement using kit 1E of Example 1 for a kit for measuring LDL-C was almost the same as the concentration of LDL-C(mg/dL) determined in measurement using MetaboLead LDL-C for a kit for measuring LDL-C. Accordingly, it has been revealed that LDL-C in a sample can be accurately measured by the method for measuring LDL-C of the present invention by use of the kit for measuring LDL-C of the present invention, comprising one or more surfactants selected from the group consisting of POE alkyl ether and POEPOP alkyl ether, and a POEPOP copolymer.

Example 5

Each kit for measuring LDL-C(kits 2A to 2D) consisting of the following first reagent and second reagent was prepared.

| First reagent | |
|---|---|
| PIPES (pH 7.0) | 50 mmol/L |
| EMSE | 0.3 g/L |
| Ascorbate oxidase | 4 kU/L |
| Second reagent | |
| PIPES (pH 7.0) | 50 mmol/L |
| 4-AA | 0.5 g/L |
| Calcium chloride | 0.1 g/L |
| Potassium ferrocyanide | 0.02 g/L |
| LPL-311 | 3 kU/L |
| CHO-CE | 2 kU/L |
| Peroxidase | 20 kU/L |
| Pluronic L-121 | 7 g/L |
| Wondersurf S-1400 | 4 g/L |

Polyoxypropylene derivatives A to D not comprising any polyoxyethylene in its molecule (see Table 3)

Comparative Example 3

Kit 2a for measuring LDL-C consisting of the following first reagent and second reagent was prepared.

| First reagent | |
|---|---|
| PIPES (pH 7.0) | 50 mmol/L |
| EMSE | 0.3 g/L |
| Ascorbate oxidase | 4 kU/L |
| Second reagent | |
| PIPES (pH 7.0) | 50 mmol/L |
| 4-AA | 0.5 g/L |
| Calcium chloride | 0.1 g/L |
| Potassium ferrocyanide | 0.02 g/L |
| LPL-311 | 3 kU/L |
| CHO-CE | 2 kU/L |
| Peroxidase | 20 kU/L |
| Pluronic L-121 | 7 g/L |
| Wondersurf S-1400 | 4 g/L |
| PEG #2000 | 3.6 g/L |

Kit 2a for measuring LDL-C of Comparative Example 3 was the same as each kit for measuring LDL-C(kits 2A to 2D) of Example 5 except that PEG #2000 was used instead of the polyoxypropylene derivative not comprising any polyoxyethylene in a molecule in the second reagent.

Example 6

Kit 2A of Example 5 was used for a kit for measuring LDL-C, a serum with intralipos added, prepared by adding intralipos to a serum, and a serum with normal saline added, prepared by adding normal saline to a serum, were used for a sample, the concentration of LDL-C in the serum with intralipos added and the concentration of LDL-C in the serum with normal saline added were determined according to the following procedure, and the influence of intralipos was evaluated.

(1) Preparation of Serum with Intralipos Added and Serum with Normal Saline Added A human serum and a 10% intralipos injection were mixed at a ratio of 9:1, thereby preparing a serum with intralipos added. Similarly, a human serum and normal saline were mixed at a ratio of 9:1 thereby preparing a serum with normal saline added.

(2) Determination of Each Concentration of LDL-C in Serum with Intralipos Added and Serum with Normal Saline Added Kit 2A of Example 5 was used for a kit for measuring LDL-C, the serum with intralipos added and the serum with normal saline added, prepared as samples according to (1), were used, and the concentration of LDL-C(mg/dL) in each of the serums was determined according to the same procedures as in (1) and (2) of Example 2.

(3) Evaluation of Influence of Intralipos in LDL-C Measurement

The influence of intralipos in LDL-C measurement using kit 2A of Example 5 was evaluated according to the following equation (II), from the concentration of LDL-C(mg/dL) in the serum with intralipos added and the concentration of LDL-C(mg/dL) in the serum with normal saline added, determined in (2) with kit 2A of Example 5 for a kit for measuring LDL-C. The results are shown in Table 3.

[Equation 2]

$$\text{Influence (\%) of intralipos in LDL-C measurement} = \frac{\text{Concentration (mg/dL) of LDL-C in serum with intralipos added}}{\text{Concentration (mg/dL) of LDL-C in serum with normal saline added}} \times 100 \quad (II)$$

Example 7

The same procedure as in Example 6 except that each kit of kits 2B, 2C, 2D and 1E of Example 5, instead of kit 2A of Example 5, was used for a kit for measuring LDL-C was performed to evaluate the influence of intralipos in measurement of LDL-C with each of the kits. The results are shown in Table 3.

Comparative Example 4

The same procedure as in Example 6 except that kit 2a of Comparative Example 3, instead of kit 2A of Example 5, was used for a kit for measuring LDL-C was performed to evaluate the influence of intralipos in measurement of LDL-C with each of the kits. The results are shown in Table 3.

TABLE 3

| Kit | | Polyoxyethylene derivative in second reagent | | Influence of intralipos |
| --- | --- | --- | --- | --- |
| | | Product name (concentration) | Structure | |
| 2A | A | Uniol D-1200 (3.6 g/L) | Polypropylene glycol | 73% |
| 2B | B | Uniol D-2000 (1.2 g/L) | | 82% |
| 2C | C | Polypropylene glycol diol type 3,000 (3.6 g/L) | | 75% |
| 2D | D | Uniol TG-3000 (3.6 g/L) | Polyoxypropylene glyceryl ether | 84% |
| 1E | — | None | — | 64% |
| 2a | — | PEG#2000 (3.6 g/L) | Polyethylene glycol | 64% |

Intralipos is a fat emulsion comprising triglyceride derived from soybean oil, as a main component, and is often used for evaluation of the influence by turbidity of lipid in a sample of a reagent for clinical examination. It is here meant that, as the ratio of the concentration of LDL-C in the serum with intralipos added, to the concentration of LDL-C in the serum with normal saline added, is closer to 100%, accurate measurement of LDL-C can be more made without any influence of intralipos.

As clear from Table 3, each kit of kits 2A to 2D of Example 5, comprising a polyoxypropylene derivative not comprising any polyoxyethylene in a molecule, had a high ratio of 70% or more of the concentration of LDL-C in the serum with normal saline added, to the concentration of LDL-C in the serum with intralipos added, as compared with kit 1E not comprising any polyoxypropylene derivative not comprising any polyoxyethylene in a molecule, and kit 2a of Comparative Example 3, comprising polyoxyethylene glycol instead of a polyoxypropylene derivative not comprising any polyoxyethylene in a molecule. Accordingly, it has been revealed that LDL-C in a sample can be accurately measured without any influence of turbidity due to lipid, by the method for measuring LDL-C of the present invention by use of the kit for measuring LDL-C of the present invention, comprising one or more surfactants selected from the group consisting of a POE alkyl ether and a POEPOP alkyl ether, a POEPOP copolymer, and a polyoxypropylene derivative not comprising polyoxyethylene in a molecule.

INDUSTRIAL APPLICABILITY

The present invention provides a method, a reagent and a kit for measuring LDL-C, which are useful for diagnosis of metabolic syndrome, arteriosclerosis, and the like.

The invention claimed is:

1. A method for measuring cholesterol in low-density lipoprotein in a sample, the method comprising:
    mixing the sample and an aqueous solvent which comprises:
        (i) a combination of cholesterol ester hydrolase and cholesterol oxidase or (ii) a combination of cholesterol ester hydrolase, an oxidized coenzyme and cholesterol dehydrogenase,
        one or more surfactants selected from the group consisting of a polyoxyethylene alkyl ether and a polyoxyethylene polyoxypropylene alkyl ether,
        a polyoxyethylene polyoxypropylene copolymer and
        a polyoxypropylene derivative not comprising any polyoxyethylene in a molecule, to react cholesterol in low-density lipoprotein in the sample with (i) the combination of cholesterol ester hydrolase and cholesterol oxidase or (ii) the combination of cholesterol ester hydrolase, an oxidized coenzyme and cholesterol dehydrogenase; and
    measuring a substance formed or consumed in the reaction from the low-density lipoprotein,
    with the proviso that the aqueous solvent does not comprise any surfactant having an alkylphenol structure.

2. The method according to claim 1, wherein the alkyl in the polyoxyethylene alkyl ether and the polyoxyethylene polyoxypropylene alkyl ether is independently an alkyl having 8 to 20 carbon atoms.

3. The method according to claim 1, wherein the polyoxypropylene derivative is a polypropylene glycol or a polyoxypropylene glyceryl ether.

4. The method according to claim 1, wherein the substance formed is a hydrogen peroxide.

5. The method according to claim 4, wherein the hydrogen peroxide is measured using a reagent for measuring hydrogen peroxide.

6. The method according to claim 1, wherein the substance formed is a reduced coenzyme.

7. The method according to claim 6, wherein the reduced coenzyme is measured using a reagent for measuring a reduced coenzyme.

8. The method according to claim 1, wherein the aqueous solvent comprises the cholesterol ester hydrolase and the cholesterol oxidase.

9. The method according to claim 8, wherein the cholesterol ester hydrolase and the cholesterol oxidase are reacted with the sample, thereby forming hydrogen peroxide.

10. The method according to claim 8, wherein alkyl in the polyoxyethylene alkyl ether and the polyoxyethylene polyoxypropylene alkyl ether is independently an alkyl having 8 to 20 carbon atoms.

11. The method according to claim 8, wherein the polyoxypropylene derivative comprises a polypropylene glycol or a polyoxypropylene glyceryl ether.

12. The method according to claim 1, wherein the aqueous solvent excludes polyoxyethylene alkyl ether.

13. The method according to claim 1, wherein the aqueous solvent comprises the polyoxyethylene polyoxypropylene alkyl ether.

14. The method according to claim 1, wherein the method excludes any removal of cholesterol in lipoprotein other than the low-density lipoprotein in a sample before measurement of the low-density lipoprotein-cholesterol.

15. The method according to claim 1, wherein the sample comprises at least one selected from the group consisting of whole blood, plasma, and serum.

16. A method for measuring cholesterol in total low-density lipoprotein in a sample, the method comprising:
   mixing the sample and an aqueous solvent which comprises:
   (i) a combination of cholesterol ester hydrolase and cholesterol oxidase or (ii) a combination of cholesterol ester hydrolase, an oxidized coenzyme and cholesterol dehydrogenase,
   one or more surfactants selected from the group consisting of a polyoxyethylene alkyl ether and a polyoxyethylene polyoxypropylene alkyl ether,
   a polyoxyethylene polyoxypropylene copolymer and
   a polyoxypropylene derivative not comprising any polyoxyethylene in a molecule, to react cholesterol in low-density lipoprotein in the sample with (i) the combination of cholesterol ester hydrolase and cholesterol oxidase or (ii) the combination of cholesterol ester hydrolase, an oxidized coenzyme and cholesterol dehydrogenase; and
   measuring a substance formed or consumed in the reaction,
   with the proviso that the aqueous solvent does not comprise any surfactant having an alkylphenol structure.

17. The method according to claim 16, wherein
   the substance formed or consumed in the reaction is measured from the low-density lipoprotein, and
   the method excludes any removal of cholesterol in lipoprotein other than low-density lipoprotein in a sample before measurement of low-density lipoprotein-cholesterol.

18. A method for measuring cholesterol in low-density lipoprotein in a sample, the method comprising:
   mixing the sample and an aqueous solvent which comprises:
   (i) a combination of cholesterol ester hydrolase and cholesterol oxidase or (ii) a combination of cholesterol ester hydrolase, an oxidized coenzyme and cholesterol dehydrogenase,
   one or more surfactants selected from the group consisting of a polyoxyethylene alkyl ether and a polyoxyethylene polyoxypropylene alkyl ether,
   a polyoxyethylene polyoxypropylene copolymer and
   a polyoxypropylene derivative not comprising any polyoxyethylene in a molecule, to react cholesterol in low-density lipoprotein in the sample with (i) the combination of cholesterol ester hydrolase and cholesterol oxidase or (ii) the combination of cholesterol ester hydrolase, an oxidized coenzyme and cholesterol dehydrogenase; and
   measuring a substance formed or consumed in the reaction,
   with the proviso that the aqueous solvent does not comprise any surfactant having an alkylphenol structure,
   wherein the method excludes any removal of cholesterol in lipoprotein other than the low-density lipoprotein in a sample before measurement of the low-density lipoprotein-cholesterol.

* * * * *